US011747352B2

(12) United States Patent
McGraw et al.

(10) Patent No.: US 11,747,352 B2
(45) Date of Patent: Sep. 5, 2023

(54) EPLERENONE FOR PHENOTYPING OF CYP3A5 ENZYME ACTIVITY IN SALIVA SAMPLES

(71) Applicant: Concordia University, Inc., Mequon, WI (US)

(72) Inventors: Joseph McGraw, Germantown, WI (US); Armin Gerhardt, Mettawa, IL (US)

(73) Assignee: Concordia University, Inc., Mequon, WI (US)

( * ) Notice: Subject to any disclaimer, the term of this patent is extended or adjusted under 35 U.S.C. 154(b) by 67 days.

(21) Appl. No.: 16/637,153

(22) PCT Filed: Aug. 7, 2018

(86) PCT No.: PCT/US2018/045618
§ 371 (c)(1),
(2) Date: Feb. 6, 2020

(87) PCT Pub. No.: WO2019/032589
PCT Pub. Date: Feb. 14, 2019

(65) Prior Publication Data
US 2020/0371123 A1 Nov. 26, 2020

Related U.S. Application Data

(60) Provisional application No. 62/542,030, filed on Aug. 7, 2017.

(51) Int. Cl.
| | | |
|---|---|---|
| G01N 33/94 | (2006.01) |
| A61K 31/4439 | (2006.01) |
| A61K 31/485 | (2006.01) |
| A61K 31/522 | (2006.01) |
| A61K 31/585 | (2006.01) |

(52) U.S. Cl.
CPC ..... G01N 33/9453 (2013.01); A61K 31/4439 (2013.01); A61K 31/485 (2013.01); A61K 31/522 (2013.01); A61K 31/585 (2013.01); C12Y 114/14001 (2013.01); G01N 2333/90245 (2013.01); G01N 2800/085 (2013.01)

(58) Field of Classification Search
CPC .................................................. G01N 33/9453
USPC ........................................................ 514/173
See application file for complete search history.

(56) References Cited

U.S. PATENT DOCUMENTS 10,927,398 B2  2/2021 McGraw et al.
2005/0233470 A1 * 10/2005 Clark .................. G01N 24/088
436/173

FOREIGN PATENT DOCUMENTS

WO    2006112513 A1   10/2006
WO    2017095921 A1    6/2017

OTHER PUBLICATIONS

Cook et al., Drug Metabolism. & Disposition (2003) vol. 31(11), pp. 1448-1455.*
Balain et al., Clin. Pharm. & Therapeutics (1995) vol. 57(6), pp. 662-669.*
Bailey et al., Acyl Glucuronide Reactivity in Perspective: Biological Consequenes, Chemico-Biological Interactions, 2003, 145:117-137.
Begas et al., In Vivo Evaluation of CYP1A2, CYP2A6, NAT-2 and Xanthine Oxidase Activities in a Greek Population Sample by the RP-HPLC Monitoring of Caffeine Metabolic Ratios, Biomedical Chromatography, 2007, 21(2):190-200.
Cook et al., Involvement of CYP3A in the Metabolism of Eplerenone in Humans and Dogs: Differential Metabolism by CYP3A4 and CYP3A5, Drug Metabolism & Disposition, 2002, 30(11):1344-1351.
Cook et al., Single- and Repeated-Dose Pharmacokinetics of Eplerenone, A Selective Aldosterone Receptor Blocker, in Rats, Xenobiotica, 2003, 33(3):305-321.
Danjuma et al., Converging Indications of Aldosterone Antagonists (Spironolactone and Eplerenone): A Narrative Review of Safety Profiles, Curr Hypertens Rep, 2014, 16:414, 10 pages.
Donzelli et al., The Basel Cocktail for Simultaneous Phenotyping of Human Cytochrome P450 Isoforms in Plasma, Saliva and Dried Blood Spots, Clinical Pharmacokinetics, 2014, 53(3):271-282.
Dorne et al., Uncertainty Factors for Chemical Risk Assessment: Human Variability in the Pharmacokinetics of CYP1A2 Probe Substrates, Food and Chemical Toxicology, 2001, 39(7):681-696.
Foti et al., Selection of Alternative CYP3A4 Probe Substrates for Clinical Drug Interaction Studies Using In Vitro Data and In Vivo Simulation, Drug Metabolism and Disposition, 2010, 38(6):981-987.
Frank et al., Evaluation of Probe Drugs and Pharmacokinetic Metrics for CYP2D6 Phenotyping, European Journal of Clinical Pharmacology, 2007, 63(4):321-333.
Hakooz, Caffeine Metabolic Ratios for the In Vivo Evaluation of CYP1A2, N-acetyltransferase 2, Xanthine Oxidase and CYP2A6 Enzymatic Activities, Current Drug Metabolism, 2009, 10(4):329-338.

(Continued)

*Primary Examiner* — Taofiq A Solola
(74) *Attorney, Agent, or Firm* — Quarles & Brady LLP

(57) ABSTRACT

Disclosed are methods and compositions which may be used in human cytochrome P450 (CYP450) enzyme phenotyping. The methods and compositions typically utilize substrate for CYP3A5 comprising eplerenone which may be administered orally to a subject. Subsequently, metabolites of eplereone may be detected in the subject's saliva as well as any non- metabolized eplerenone to calculate a metabolic ratio for CYP3A5 enzyme in order to generate a phenotypic CYP3A5 enzyme profile for the subject.

8 Claims, 13 Drawing Sheets

(56) References Cited

OTHER PUBLICATIONS

Isoherranen et al., The Influence of CYP3A5 Expression on the Extent of Hepatic CYP3A Inhibition is Substrate-Dependent: An In Vitro-In Vivo Evaluation, Drug Metabolism & Disposition, 2008, 36(1):146-154.
Jurica et al., Chapter 8: Determination of Cytochrome P450 Metabolic Activity Using Selective Markers, in Topics on Drug Metabolism, 2012, pp. 191-220.
Kamdem et al., Contribution of CYP3A5 to the In Vitro Hepatic Clearance of Tacrolimus, Clinical Chemistry, 2005, 51(8):1374-1381.
Nolin et al., Stereoselective Determination of the CYP2C19 Probe Drug Mephenytoin in Human Urine by Gas Chromatography-Mass Spectrometry, Journal of Chromatography B, 2003, 783(1):265-271.
Nyeki et al., Extractionless Method for the Simultaneous High-Performance Liquid Chromatographic Determination of Urinary Caffeine Metabolites for N-acetyltransferase 2, Cytochrome P450 1A2 and Xanthine Oxidase Activity Assessment, Journal of Chromatography B, 2001, 755(1-2):73-84.
Ou-Yang et al., Phenotypic Polymorphism and Gender-Related Differences of CYP1A2 Activity in a Chinese Population, British Journal of Clinical Pharmacology, 2000, 49(2):145-151.
Patki et al., In Vitro Metabolism of Midazolam, Triazolam, Nifedipine, and Testosterone by Human Liver Microsomes and Recombinant Cytochromes P450: Role of CYP3A4 and CYP3A5, Drug Metabolism and Disposition, 2003, 31(7):938-944.
Prot et al., Performance of Biotransformation of Human Primary Hepatocytes Exposed to a Pharmacological Cocktail Inside a Liver Microchip, 14th International Conference on Miniaturized Systems for Chemistry and Life Sciences, Oct. 3-7, 2010, Groningen, The Netherlands, pp. 157-159.
Rasmussen et al., Selective Effects of Somatostatin Analogs on Human Drug-Metabolizing Enzymes, Clinical Pharmacology & Therapeutics, 1998, 64(2):150-159.
Rendic, Summary of Information on Human CYP Enzymes: Human P450 Metabolism Data, Drug Metabolism Reviews, 2002, 34(1-2):83-448.
Shelepova et al., PI-49: Effect of Oral Contraceptives (OCs) on Drug Metabolizing Enzymes (DMES) as Measured by the Validated Cooperstown 5+1 Cocktail (5+1), Clinical Pharmacology and Therapeutics, 2003, 73(2):P14.
Streetman et al., Combined Phenotypic Assessment of CYP1A2, CYP2C19, CYP2D6, CYP3A, N-acetyltransferase-2, and Xanthine Oxidase with the "Cooperstown Cocktail", Clinical Pharmacology and Therapeutics, 2000, 68(4):375-383.
Streetman et al., Phenotyping of Drug-Metabolizing Enzymes in Adults: A Review of In-Vivo Cytochrome P450 Phenotyping Probes, Pharmacogenetics, 2000, 10(3):187-216.
Takata et al., Phenotype-Genotype Analysis of CYP1A2 in Japanese Patients Receiving Oral Theophylline Therapy, European Journal of Clinical Pharmacology, 2006, 62(1):23-28.
Tassaneeyakul et al., Caffeine Metabolism by Human Hepatic Cytochromes P450: Contributions of 1A2, 2E1 and 3A Isoforms, Biochemical Pharmacology, 1994, 47(10):1767-1776.
Tenneze et al., Assessment of CYP2D6 and CYP2C19 Activity In Vivo in Humans: A Cocktail Study with Dextromethorphan and Chloroguanide Alone and in Combination, Clinical Pharmacology & Therapeutics, 1999, 66:582-588.
Van Troostwijk et al., Two Novel Methods for the Determination of CYP1A2 Activity Using the Paraxanthine/Caffeine Ratio, Fundamental & Clinical Pharmacology, 2003, 17(3):355-362.
Videau et al., Biochemical and Analytical Development of the CIME Cocktail for Drug Fate Assessment in Humans, Rapid Communications in Mass Spectrometry, 2010, 24(16):2407-2419.
Woillard et al., Tacrolimus Updated Guidelines Through popPK Modeling: How to Benefit More from CYP3A Pre-emptive Genotyping Prior to Kidney Transplantation, Frontiers in Pharmacology, 2017, vol. 8, Article 358, 14 pages.
Xiang et al., The Influence of CYP3A5*3 and BCRPC421A Genetic Polymorphisms on the Pharmacokinetics of Felodipine in Healthy Chinese Volunteers, Journal of Clinical Pharmacy and Therapeutics, 2017, 42(3):345-349.
Zanger et al., Cytochrome P450 2D6: Overview and Update on Pharmacology, Genetics, Biochemistry, Naunyn-Schmiedeberg's Archives of Pharmacology, 2004, 369(1):23-37.
Zhou, Polymorphism of Human Cytochrome P450 2D6 and Its Clinical Significance, Clinical Pharmacokinetics, 2009, 48(11):689-723.
PCT International Search Report and Written Opinion, PCT/US2018/045618, dated Nov. 22, 2018, 8 pages.
European Patent Office, Extended European Search Report, Application No. 18842984.9, dated Apr. 6, 2021, 8 pages.

* cited by examiner

EPLERENONE FOR PHENOTYPING OF CYP3A5 ENZYME ACTIVITY IN SALIVA SAMPLES

CROSS-REFERENCE TO RELATED PATENT APPLICATIONS

The present application is the U.S. national stage entry of International Application No. PCT/US2018/045618 filed Aug. 7, 2018, which application claims the benefit of priority under 35 U.S.C. § 119(e) to U.S. Provisional Application No. 62/542,030, filed on Aug. 7, 2017, the content of which is incorporated herein by reference in its entirety.

BACKGROUND

The field of the invention relates to medical diagnostics. More particularly, the field of the invention relates to pharmacogenetic medical diagnostics and personalized medicine. More particularly, the field of the invention relates to the use of eplerenone which may be utilized in methods for phenotyping of CYP3A5 enzyme activity in a saliva sample.

Cytochrome P450 (CYP450) enzymes are responsible for much of the variability in drug response and toxicity susceptibility. The fields of pharmacogenetics and later pharmacogenomics began with observations that individuals from different racial/ethnic groups experienced different rates of response and toxicity to certain drugs. Scientists found significant differences in metabolic clearance of these 'highly variable' drugs on an individual and population level. They also found disproportionate frequencies of individuals with very low metabolic clearance amongst different racial/ethnic groups. Further investigations revealed genetic variants resulted in altered CYP450 enzyme activity and therefore differences in metabolic clearance of the drugs. After many years of investigation, CYP450 enzyme activity has remained the dominant determinant of metabolic clearance for many drugs. The CYP450 enzyme family is the most studied enzyme family in the field of pharmacogenetics.

When a drug is primarily metabolized via a specific CYP450 enzyme (i.e. responsible for 80% or more of drug clearance) it is known as a 'probe drug'. For these particular drugs, alterations in CYP450 enzyme activity results in significant differences in drug clearance. Differences in metabolic enzyme activity are quantified by measuring the metabolic ratio i.e. the concentration or area ratio of a known enzyme substrate divided by the primary metabolite. The metabolic ratio of the probe substrate is also called the metabolic phenotype although metabolic phenotype is often expressed as a categorical value such as poor metabolizer. Currently there are genetic assays which predict metabolic phenotype based on the presence or absence of genetic variants which result in altered metabolic clearance. The predicted metabolic phenotypes based on genetic analyses are categorical and labeled relative to an average individual being labeled an extensive metabolizer. Other designations vary by CYP450 enzyme and particular study but common designations include: extensive metabolizer (EM) (i.e. the average wild type individual), poor metabolizer (PM) (i.e. individuals who have very poor metabolic clearance relative to the average wild type), intermediate metabolizer (IM) (i.e. individuals who have metabolic clearance between the average wild type and a poor metabolizer phenotype), rapid metabolizer (RM) (i.e. individuals who have higher metabolic clearance relative to the average wild type individual), and ultra-rapid metabolizers (UM) (i.e. individuals who have metabolic clearance significantly higher than rapid metabolizers).

Once the metabolic phenotype is determined, interventions such as avoiding specific drugs in high risk metabolizer phenotypes, lowering drug dosages in poor metabolizers, or raising drug dosages in rapid metabolizers. There is evidence showing benefits of genetic predicted phenotype guided drug dosing. However, there are some drawbacks to using genetic predicted phenotype. The genes encoding CYP450 enzymes do not change throughout a person's life but their level of expression, translation and activity do, thus the resulting metabolic phenotype is altered. A multitude of physiological and environmental factors such as alcohol ingestion, aging, diet, drug/pharmaceutical use producing enzyme induction or inhibition (drug-drug interactions), hepatic disease, renal disease, etc. impact the metabolic phenotype. In-vitro studies show a complex regulation of CYP450 activity including transcriptional regulation, translational regulation, post transcriptional modifications, and protein-protein interactions.

To avoid the pitfalls associated with genetic prediction of metabolic phenotype we have developed compositions, methods, and kits for the direct testing of a metabolic phenotype for CYP3A5 enzyme activity using eplerenone as a substrate in a non-invasive saliva based testing assay. Eplerenone, which itself is an extremely safe phenotyping probe, may be used as part of a mélange of additional extremely safe phenotyping probes for additional CYP450 enzyme activity in the non-invasive saliva based testing assay. The compositions, methods, and kits disclosed herein allow for direct measurement of a metabolic phenotype for CYP3A5 enzyme activity which can be converted into a traditional categorical phenotype or can be reported as a continuous variable metabolic phenotype.

SUMMARY

Disclosed are methods and compositions which may be used in cytochrome P450 (CYP450) enzyme phenotyping. The methods and compositions typically utilize a composition comprising eplerenone as a substrate for CYP3A5 enzyme which may be administered orally to a subject. Subsequently, metabolites of eplerenone whose metabolism or degradation is catalyzed by CYP3A5 may be detected in the subject's saliva as well as any non-metabolized eplerenone to calculate a metabolic ratio for CYP3A5 enzyme in order to generate a phenytopic CYP3A5 enzyme profile for the subject. The phenytopic CYP3A5 enzyme profile for the subject may be utilized in order to dose a drug for a subject and/or to assess hepatic function in the subject, for example, in a subject experiencing or at risk for developing hepatic failure.

DETAILED DESCRIPTION

Figure 1:
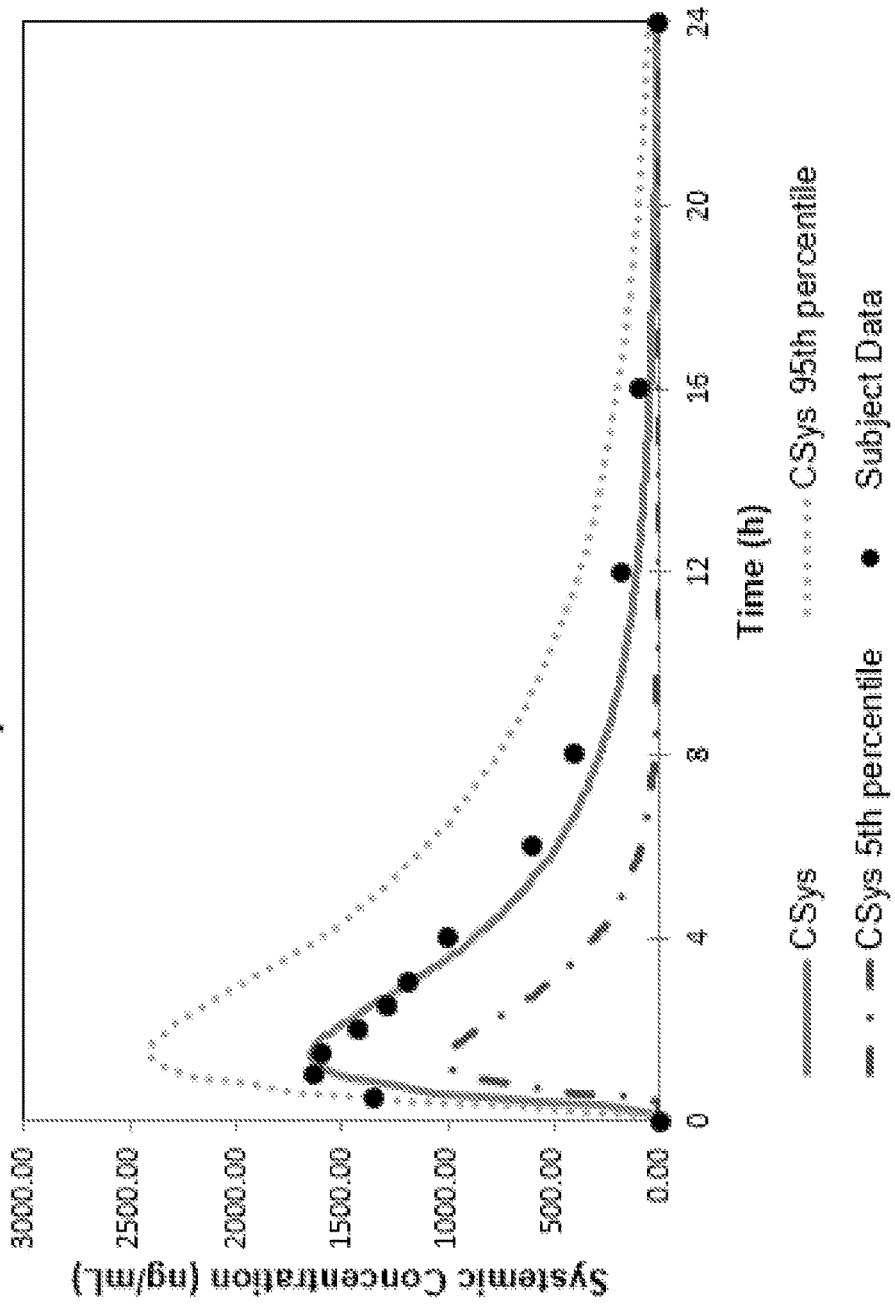
FIG. 1 shows the SimCYP average modeled eplerenone concentration versus time profile agrees with average concentration versus time concentrations reported in the prior art for a 100 mg eplerenone dose. (See Cook, C. S., L. M. Berry, R. H. Bible, J. D. Hribar, E. Hajdu and N. W. Liu (2003). "Pharmacokinetics and metabolism of [14C]eplerenone after oral administration to humans." *Drug Metab Dispos* 31(11): 1448-1455; the content of which is incorporate herein by reference in its entirety).

The present invention is described herein using several definitions, as set forth below and throughout the application.

Unless otherwise specified or indicated by context, the terms "a", "an", and "the" mean "one or more." For example, "a substrate" and "a metabolite" should be interpreted to mean "one or more substrates" and "one or more metabolites," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, "a subject in need thereof" may include a subject in need of phenotyping for cytochrome P450 (CYP450) enzymes. The term "subject" may be used interchangeably with the terms "patient" and "individual." A "subject" is intended to include human and non-human animals (e.g., non-human primates, dogs, cats, horses, and the like).

As used herein, "a subject in need thereof" may include a subject in need of drug dosing. As such, the disclosed methods may include methods for determining an appropriate dose for a drug for a subject based on the subject's phenotype for one or more cytochrome P450 (CYP450) enzymes, which phenotype may be determined as disclosed herein.

As used herein, "a subject in need thereof" may include a subject experiencing or at risk for developing hepatic failure. As such, the disclosed methods may include methods of assessing liver function in a subject experiencing or at risk for developing hepatic failure based on the subject's phenotype for one or more cytochrome P450 (CYP450) enzymes, which phenotype may be determined as disclosed herein.

As used herein, "a subject in need thereof" may include a subject enrolled in a drug study. As such, the disclosed methods may include methods of assessing liver function in a subject prior to participation in a drug study based on the subject's phenotype for one or more cytochrome P450 (CYP450) enzymes, which phenotype may be determined as disclosed herein.

The compositions disclosed herein typically include one or more substrates for one or more one or more isoforms of the cytochrome P450 (CYP450) enzymes. The disclosed compositions may include a mélange of substrates. As used herein, the term "mélange" means a mixture, and the terms "mélange" and "mixture" may be used interchangeably herein. A mélange may include a mixture of substrates for one or more enzymes. In particular, a mélange may include a mixture of substrates for one or more isoforms of the cytochrome P450 (CYP450) enzymes. The substrates of the mixture may be individually formulated into multiple formulations which may be administered substantially concurrently and/or the substrates of the mixture may be formulated together into a single formulation.

As used herein, a "substrate" refers to a chemical compound that is recognized by an enzyme and for which the enzyme catalyzes conversion of the substrate into a different chemical compound which may be referred to as a "metabolite." For example, the liver contains enzymes that convert various drug substances (i.e. substrates) to metabolites, which are eliminated from the body in urine or excrement. This enzyme conversion process often determines the duration of action or intensity of drugs, which is why some drugs may be taken several times each day to treat diseases and produce desirable pharmacological effects.

The term "converted" refers to a substrate that has been converted to a metabolite. The term "converted may be used interchangeably herein with the term "metabolized," and the term "unconverted" may be used interchangeably herein with the term "non-metabolized."

Liver enzymes may include isoforms of cytochrome P450 (CYP450), N-acetyl transferases, UDP-glucuronosyltransferases, oxidases sulfotransferases and other enzymes. Each of these enzyme systems may be comprised of numerous isoforms, each of which is capable of metabolizing different substrates. For example, the CYP450 system in the human liver includes at least ten individual isoforms. The CYP450 isoforms are often critical in determining the rate of elimination of drugs, and metabolism by CYP isoforms often represents the rate-limiting step in elimination of pharmaceuticals. Prediction of metabolic phenotype based exclusively on genetic analysis, genetic markers, and/or genetic deficiencies may produce an imprecise result due to failure to include environmental factors, concomitant disease, levels of CYP450 isoform expression, translation and activity, and other factors.

As such, a subject's ability to metabolize a pharmaceutical is an important factor in determining a proper dose or dose regimen for the pharmaceutical. Metabolic activity may be based on genetic markers including genetic deficiencies in a CYP450 isoform. As such, metabolic activity may be assessed by performing a genetic analysis. However, genetic analysis has not proven sufficiently useful to be routinely adopted in current medical practice.

As such, an understanding of the subject's actual metabolic activity is the most important factor for determining a proper dose or dose regimen for the pharmaceutical. The methods disclosed herein may include determining a subject's methabolic phenotype and/or characterizing the subject's metabolic activity. A subject's metabolic activity may be referred to herein as a "metabolic phenotype." Based on a metabolic phenotype, a subject may be characterized as a poor metabolizer (PM), and intermediate metabolizer (IM), an extensive metabolizer (EM), or an ultra-rapid metabolizer (UM). For example, metabolic phenotypes may be generated by administering a substrate for an enzyme to the subject. Subsequently, a sample may be taken from the subject and analyzed for the presence of a metabolite and any unconverted or non-metabolized substrate to calculate a metabolic ratio, which can be used to characterize the subject's metabolic activity.

Compositions for CYP3A5 Phenotyping Using Saliva Samples

As such, disclosed herein are methods and compositions which may be used in human cytochrome P450 (CYP450) enzyme phenotyping. The methods and compositions may include or utilize one or more substrates for one or more different CYP450 enzymes, but in particular, the methods and compositions may include or utilize one or more substrates for CYP3A5 such as eplerenone, which may be administered orally to a subject. The methods and compositions may include or utilize one or more additional substrates for CYP450 enzymes (e.g., one or more substates for one or more of CYP1A2, CYP2C9, CYP2C19, CYP2E1, CYP2D6, and CYP3A4) which may be administered orally to a subject. The substrates of the disclosed compositions may be administered orally to a subject. Subsequently, for example, after 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 24.0 hours or later, a saliva sample from the subject may be tested for a metabolite of one or more substrates of the composition that are metabolized by one or more CYP450 isoforms to generate the metabolite. The saliva sample from the subject also may be tested for any non-metabolized substrate. As such, a ratio of the concentration of metabolite/non-metabolized substrate in saliva from the subject may be calculated to generate a metabolic phenotype for the subject for one or more CYP450 isoforms.

The disclosed methods typically include administering, typically orally, to a subject in need thereof a composition comprising a substrate for CYP3A5 ($SUB_{CYP3A5}$), wherein CYP3A5 catalyzes conversion of $SUB_{CYP3A5}$ to a metabolite ($MET_{CYP3A5}$). Typically, the substrate for CYP3A5 ($SUB_{CYP3A5}$) is eplerenone and the metabolite(s) ($MET_{CYP3A5}$) include 6β-hydroxyeplerenone and/or 21-hydroxyeplerenone. Subsequently, the methods may include detecting in a saliva sample from the subject $MET_{CYP3A5}$ (e.g., 6β-hydroxyeplerenone and/or 21-hydroxyeplerenone) and unconverted $SUB_{CYP3A5}$ (e.g., eplerenone).

In some embodiments, the disclosed methods may include administering, typically orally, to a as subject in need thereof a composition comprising one or more additional substrates for one or more additional CYP450 enzymes. For example, the disclosed methods may include administering, typically orally, to a subject in need thereof a composition comprising one or more additional substrates such as: (i) a substrate for CYP1A2 ($SUB_{CYP1A2}$), wherein CYP1A2 catalyzes conversion of $SUB_{CYP1A2}$ to a metabolite ($MET_{CYP1A2}$); (ii) a substrate for CYP2C19 ($SUB_{CYP2C19}$), wherein CYP2C19 catalyzes conversion of $SUB_{CYP2C19}$ to a metabolite ($MET_{CYP2C19}$), (iii) a substrate for CYP2D6 ($SUB_{CYP2D6}$), wherein $CYP_{2D6}$ catalyzes conversion of $SUB_{CYP2D6}$ to a metabolite ($MET_{CYP2D6}$); and/or (iv) a substrate for CYP3A4 ($SUB_{CYP3A4}$), wherein CYP3A4 catalyzes conversion of $SUB_{CYP3A4}$ to a metabolite ($MET_{CYP3A4}$); and/or (v) a substrate for CYP3A5 ($SUB_{CYP3A5}$), wherein CYP3A5 catalyzes conversion of $SUB_{CYP3A5}$ to a metabolite ($MET_{CYP3A5}$). Subsequently, the methods may include detecting in a saliva sample from the subject one or more of: (i) $MET_{CYP1A2}$ and unconverted $SUB_{CYP1A2}$; (ii) $MET_{CYP2C19}$ and unconverted $SUB_{CYP2C19}$; (iii) MET CYP2D6 CYP2D6 and unconverted $SUB_{CYP2D6}$; and/or (iv) $MET_{CYP3A4}$ and unconverted $SUB_{CYP3A4}$.

In the disclosed methods, the composition administered to the subject may comprise a tablet formulation of a substrate for CYP3A5 ($SUB_{CY3A5}$) such as eplerenone. Suitable tablet formulations may include immediate release tablet formulations, for example an immediate tablet release formulation for a substrate for $SUB_{CY3A5}$ such as eplerenone. In some embodiments, the tablet formulations may include a non-substrate coating (e.g., an enteric coating or other type of coating). In some embodiments, the tablet formulations are coated in order to prevent and/or minimize the quantity of substrate lost during the process of swallowing.

In some embodiments, the composition administered to the subject may comprise additional tablet formulations of one or more substrates selected from $SUB_{CYP1A2}$, $SUB_{CYP2C19}$, $SUB_{CYP2D6}$, and/or $SUB_{CY3A4}$. In some embodiments, the composition includes multiple tablets, for example, one tablet of $SUB_{CY3A5}$ such as eplerenone, and in addition one tablet of one or more of $SUB_{CYP1A2}$, $SUB_{CYP2C19}$, $SUBC_{YP2D6}$, and/or $SUB_{CY3A4}$. In other embodiments, the composition administered to the subject may comprise a single tablet formulation, the single tablet formulation including $SUB_{CY3A5}$ such as eplerenone, and in addition, the single tablet formulation including each of substrates including $SUB_{CYP1A2}$, $SUB_{CYP2C19}$, $SUB_{CYP2D6}$, and/or $SUB_{CY3A4}$. Suitable tablet formulations may include immediate release tablet formulations, for example an immediate tablet release formulation for $SUB_{CY3A5}$ such as eplerenone, and in addition, and an immediate table release formulation for each of $SUB_{CYP1A2}$, $SUB_{CYP2C19}$, $SUB_{CYP2D6}$, and/or $SUB_{CY3A4}$. In some embodiments, the tablet formulations may include a non-substrate coating (e.g., an enteric coating or other type of coating).

In some embodiments, the composition administered in the disclosed methods is a buffered composition. For example, the composition administered in the disclosed methods may include a basic buffering agent, which may include but is not limited to sodium bicarbonate and/or calcium carbonate.

In some embodiments, the composition administered in the disclosed methods has a basic pH when the composition is dissolved in water. For example, the composition administered in the disclosed methods may have a pH greater than about 7.5, 8.0, 8.5, or 9.0 when dissolved in water.

In the disclosed methods, the metabolites and/or the unconverted substrates may be detected in saliva using any suitable procedure. Suitable procedures may include but are not limited to procedures selected from the group consisting of Ultra High Pressure Liquid Chromatography (UHPLC), Mass Spectroscopy (MS), High Pressure Liquid Chromatography (HPLC), Ultraviolet Spectroscopy (UV), Gas Chromatography (GC), Electron Capture Detection (ECD), Flame Ionization Detection (FID), Raman Infrared (RI) Spectroscopy, Matrix-Assisted Laser Desorption/Ionization (MALDI), immunoassay analytical techniques, and combinations thereof. In addition, in the disclosed methods the metabolites and/or the unconverted substrates may be detected in saliva using reagent composition that include one or more reagents for detecting the metabolites and/or the unconverted substrates via reacting the saliva with the reagent compositions.

In the disclosed methods, the composition administered to the subject typically includes a substrate for CYP3A5 ($SUB_{CY3A5}$), such as eplerenone. In some embodiments, the composition administered to the subject may include a substrate for one or more additional isoforms of CYP. In some embodiments, a substrate of the composition is a substrate for more than one isoform of CYP (e.g., a substrate for CYP3A5 may additionally be a substrate for CYP3A4 and/or a substrate for CYP3A4 may additional be a substrate for CYP3A5). In other embodiments, a substrate of the composition is a substrate for one isoform of CYP and is not a substrate for another or any other isoform of CYP (e.g., a substrate for CYP3A5 may not be a substrate for CYP3A4 and/or a substrate for CYP3A4 may not be a substrate for CYP3A5).

The substrates of the compositions that are administered in the disclosed methods may include "drugs" as known in the art. Preferably, the substrates (i.e., drugs) of the compositions that are administered in the disclosed methods and the metabolites of the subtrates have suitable pharmaceutical characteristics such as oral bioavailability (e.g., greater than about 20%, 30%, 40% 50%, 60%, 70%, 80%, 90% or lower), and low or no plasma protein binding (e.g., less than about 90%, 80%, 70%, 60%, 50%, 40%, 30%, or 20%, or lower). Preferably, the substrates and the metabolites of the substrates have a suitable half-life which, in some embodiments, may be a half-life of greater than about 0.5, 1.0, or 2.0 hours and less than about 8.0, 7.0, 6.0, 5.0, or 4.0 hours (e.g., a half life of 2.0-4.0).

In the disclosed methods, the compositions administered to the subject typically include a substrate for CYP isoform 3A5 ($SUB_{CYP3A5}$), for example, wherein a metabolite ($MET_{CYP3A5}$) is subsequently detected in saliva of the subject and any unmetabolized $SUB_{CYP3A5}$. Suitable substrates for CYP3A5 may include but are not limited to eplerenone (e.g., where the metabolite ($MET_{CYP33A4}$) is 6β-hydroxyeplerenone and/or 21-hydroxyeplerenone). Other suitable substrates for CYP3A5 may include but are not limited to alprazolam (α-hydroxylation), cortisol, alfentanil, midazolam, tacrolimus, and triazolam, and vincristine.

Suitable substrates for additional CYP450 enzymes for assessing metabolism of CYP450 enzyme activity in saliva may include one or more drugs listed in the following Tables of Exemplary Drugs:

Table of Exemplary Drugs for Assessing Metabolism by CYP1A2.

| DRUG | ORAL BIOAVAILABILITY | PLASMA PROTEIN BINDING | HALF LIFE (hrs) | MOLECULAR WEIGHT | METABOLISM |
|---|---|---|---|---|---|
| Amitriptyline | ~43-46% | >90% | ~13-36 | 277.4 | 2D6 |
| Clomipramine | 20-78% | 97% | 19-37 | 314.85 | 2C19, 3A4 |
| Imipramine | 22-77% | 60-96% | 8-21 | 280.41 | 2D6 |
| Agomelatine | <5% | 95% | 1-2 | 243.3 | |
| Clozapine | 12-81% | 97% | 4-66 | 326.82 | 2D6, 3A4 |
| Olanzapine | 87% | 93% | 21-54 | 312.43 | 2D6 |
| Haloperidol | 60% | 88.4-92.5% | 14-37 | 375.86 | 1A2, 2D6 |
| Caffeine | | 17-36% | 5 | 194.19 | |
| Ropivacaine | 87-98% - IV | 94% | 5-7 | 274.4 | |
| Theophylline | ~100% | 40% | 1.5-9.8 | 180.16 | 2E1 |
| Zolmirripran | ~40% | 25% | 3 | 287.36 | |
| Melatonin | 3-76% | | 35-50 min | 232.28 | 1A1, 2C19 |
| Tamoxifen | | 99% | ~5-7 days | 371.51 | 2C9, 3A4, 3A5, 2C19, 2D6, 1A1, 3A7, 2B6, 2B1 |
| Erlotinib | 60-100% | 93% | 36.2 | 393.44 | 3A4, 1A1, 1C |
| Cyclobenzaprine | 33-55% | 93% | 8-37 | 275.39 | 2D6, 3A4 |
| Estradiol | 43% | >95% | 36 hours | 272.38 | 3A4 |
| Fluvoxamine | 53-84% | ~77-80% | ~14-16 | 318.33 | |
| Mexiletine | 90% | 50-60% | 10-12 | 179.26 | 2D6 |
| Naproxen | 95% | >99% | 8-21 | 230.26 | 2C9, 2C8 |
| Ondansetron | 100% | 70-76% | 3-6 | 293.36 | 2D6, 3A4 |
| Phenacetin | | | | 179.22 | |
| Paracetamol | 85-98% | 10-25% | 1-4 | 151.16 | 2D6, 2E1 |
| Propranolol | 100% | >90% | 4 | 259.34 | 2D6 |
| Riluzole | ~60% | 96% | 12 | 234.2 | |
| Tacrine | 2.4-36% | 55% | 2-4 | 198.26 | |
| Tizanidine | 40% | 30% | 2.5 | 253.71 | |
| Verapamil | 20-35% | 90% | 2.8-7.4 | 454.6 | 2C8, 2C18, 2C9, 3A4, 3A5, 2C9, 2C8 2C18, 2C19, 1A1, |
| Warfarin | 100% | 99% | 20-60 | 308.33 | 3A4, |
| Zileuton | | 93% | 2.5-3.2 | 236.29 | 2C9, 3A4 |

Table of Exemplary Drugs for Assessing Metabolism by CYP2C9.

| DRUG | ORAL BIOAVAILABILITY | PLASMA PROTEIN BINDING | HALF LIFE (hrs) | MOLECULAR WEIGHT | METABOLISM |
|---|---|---|---|---|---|
| Celecoxib | | 97% | 11 | 381.38 | |
| Lomoxicam | IM: 87% | 99.7% | 4 | 371.8 | |
| Diclofenac | 50% | >99% | 1.9-2.2 | 296.15 | |
| Ibuprofen | 87-100% | 99% | 1.8-2.44 | 206.3 | |
| Naproxen | 95% | >99% | 12-17 | 230.26 | |
| Ketoprofen | 90% | >99% | 2.1 | 254.29 | |
| Piroxicam | | 99% | 50 | 331.348 | |
| Meloxicam | 89% | 99.4% | 15-20 | 351.4 | |
| Suprofen | 92% | >99% | 2-4 | 260.3 | |
| Phenytoin | 20-90% | 88-93% | 14-22 | 274.25 | 2C9, 2C19 |
| Fluvastatin | 24% | 98% | 2.5 | 411.5 | 2C9, 2C8, 3A4 |
| Glipizide | 90-100% | 98-99% | 2-5 | 445.55 | |
| Glibenclamide | | 99% | 10 | 493.99 | |
| Glimepiride | 100% | >99% | 5-9.2 | 490.62 | |
| Tolbutamide | | 80-99% | 4.5-6.5 | 270.35 | |
| Glyburide | | 99% | 10 | 493.99 | |
| Irbesartan | 60-80% | 90% | 11-15 | 428.5 | |
| Losartan | 33% | 1.3% | 2 | 461 | 2C9, 3A4 |
| S-warfarin | 100% | 99% | 40 | 330.31 | 2C9, 2C19, 2C18, 1A2, 3A4 |
| Sildenafil | 41% | 96% | 4 | 666.7 | 3A4, 2C9 |
| Terbinafine | 40% | >99% | 22-26 | 327.9 | 2C9, 1A2, 3A4, 2C8, 2C19 |
| Amitriptyline | 30-60% | >90% | 15 | 313.87 | 3A4, 2C9, 2D6, 1A2, 2C19 |
| Fluoxetine | 60-80% | 94.5% | 4-6 days | 309.3 | 2D6, 2C9 |
| Nateglinide | 73% | 98% | 1.5 | 317.423 | 2C9. 3A4 |
| Rosiglitazone | 99% | 99.8% | 3-4 | 357.4 | 2C8, 2C9 |
| Tamoxifen | | 99% | 5-7 days | 371.5 | 3A, 2C9, 2D6 |
| Torasemide | 80% | >99% | 2.2-3.8 | 348.43 | |
| Ketamine | IM: 90-93%, PO: 16% | 47% | 2-3 | 274.19 | |
| THC | 10-35% | 97-99% | 1.6-59 | 314.469 | 2C9, 2C19, 3A4 |
| Limonene | | | | 136.24 | 2C9, 2C19 |
| Tapentadol | 32% | 20% | 4-5 | 257.8 | 2C9, 2D6 |
| Polyunsaturated FAs | | | | | |
| Montelukast | 64-73% | >99% | 2.7-5.5 | 608.18 | 2C8, 2C9, 3A4 |

Table of Exemplary Drugs for Assessing Metabolism by CYP2C19.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Amitriptyline | 30-60% | >90% | 15 | 313.87 | 3A4, 2C9, 2D6, 1A2, 2C19 |
| Clomipramine | 20-78% | 97% | 32 | 351.3 | |
| Imipramine | 94-96% | 89% | 6-18 | 316.9 | 2C19, 2D6 |
| Citalopram | 80% | 80% | 35 | 324.4 | 3A4 |
| Moclobemide | 55-95% | 50% | 2 | | |
| Bupropion | | 84% | 19-21.3 | 276-320 | 2B6 |
| Diazepam | 98% | 95-99.3% | Up to 48 | 284.75 | 3A4 |
| Mephenytoin | "Well-absorbed" | 59.6% | 17 | 218.25 | |
| Nordazepam | | | 36-200 | 270.7 | |
| Phenytoin | 20-90% | 88-93% | 14-22 | 274.25 | 2C9 |
| Phenobarbital | 80-100% | 20-60% | 36-120 | 232.24 | |
| Primidone | 90-100% | 20-30% | 3.3-7 | 218.25 | |
| Hexobarbital | | 25% | | 236.3 | 2C9 |
| Methylphenobarbital | 50% | 70-76% | 11-67 | 246.3 | |
| Llansoprazole | 81-91% | 97-99% | 0.9-1.5 | 369.37 | 1A2 |
| Omeprazole | 30-40% | 95-96% | 0.5-1 | 345.42 | |
| Pantoprazole | 77% | 98% | 1 | 405-432 | 3A4, 2D6, 2C9 |
| Rabeprazole | 52% | 96.3% | 1-2 | 381.43 | 3A |
| Esomeprazole | 90% | 97% | 1.5 | 367.4 | 3A4 |
| Clopidogrel | >50% | 98% | 6 | 419.9 | 3A, 2B6, 1A2 |
| Proguanil | | 75% | 12-18 | 253.7 | |
| Propranolol | 30-70% | 93% | 3-6 | 295.8 | |
| Limonene | | | 12-24 | 136.26 | |
| Gliclazide | 80% | 85-99% | 8-12 | 323.4 | |
| Carisoprodol | | 60% | 8 | 260.3 | |
| Chloramphenicol | 90-100% | 50-80% | 1.6-3.3 | 323.13 | |

Table of Exemplary Drugs for Assessing Metabolism by CYP2C19.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Cyclophosphamide | >75% | >60% | 3-12 | 279.1 | |
| Indomethacin | 100% | 99% | 4.5 | 357.8 | |
| Nelfinavir | | 98% | 3.5-5 | 567.78 | 3A, 2C19 |
| Nilutamide | | 80-84% | 38-59.1 | 317.2 | |
| Progesterone | 10-15% | 96-99% | PV: 5-20 min | 314.5 | |
| Teniposide | | >99% | 5 | 656.6 | |
| Warfarin | 100% | 99% | 40 | 330.31 | 2C9, 2C19, 2C18, 1A2, 3A4 |
| Tapentadol | 32% | 20% | 4-5 | 257.8 | 2C9, 2C19 |

Table of Exemplary Drugs for Assessing Metabolism by CYP2D6.

| DRUG | ORAL BIOAVAILABILITY | PLASMA PROTEIN BINDING | HALF LIFE (hrs) | MOLECULAR WEIGHT | METABOLISM |
|---|---|---|---|---|---|
| Imipramin | 94-96% | 89% | 6-18 | 316.9 | 2C19, 2D6 |
| Amitriptyline | ~43-46% | >90% | ~13-36 | 277.4 | 3A4, 2C9, 2D6, 1A2, 2C19 |
| Fluoxetine | 60-80% | 94.5% | 4-6 days | 309.3 | 2D6, 2C9 |
| Paroxetine | | 93-95% | 15-21 | 329.3 | |
| Fluvoxamine | 53% | 80% | 15.6 | 318.3 | 1A2, 2C9, 2C19, 2D6, 3A4 |
| Venlafaxine | 12.6% | 27-30% | 5 | 277 | |
| Duloxetine | 30-80% | >90% | 12 | 333.88 | 1A2, 2D6 |
| Mianserin | 20-30% | 90% | 1.4 | 264.4 | |
| Mirtazapine | 50% | 85% | 26-37 | 265.36 | 2D6, 1A2, 3A4 |
| Codeine | 90% | 7-25% | 2.5-3 | 299.36 | 2D6, 3A4 |
| Tramadol | 75% | 20% | 5.5-6.7 | 299.8 | 2D6, 3A4 |
| O-desmethyltramadol | | | 9 | 249.349 | M1 |
| N-desmethyltramadol [inactive] | | | | | |
| Oxycodone | 60-87% | 45% | 5.6 | 315.37 | 3A4, 2D6 |
| Hydrocodone | 25% | 19-45% | 7-9 | 494.5 | 3A4, 2D6, 2C19, 2B6 |
| Tapentadol | 32% | 20% | 4-5 | 257.8 | 2C9, 2D6 |
| Haloperidol | 60% | 88.4-92.5% | 14-37 | 375.86 | 1A2, 2D6 |
| Risperidone | 70% | 90% | 3-20 | 410.49 | |
| Perphenazine | 20% | | 9-12 | 403.97 | |
| Thioridazine | | | 21-24 | 370.577 | |
| Zuclopenthixol | 49% | 98% | 20 | 400.965 | 2D6, 3A4 |
| Iloperidone | 96% | 95% | 18-33 | 426.48 | 3A4, 2D6 |
| Aripiprazole | 87% | >99% | 75 | 448.38 | 2D6, 3A4 |
| Chlorpromazine | 32% | 90-99% | 6 | 318.86 | |
| Levomepromazine | 50-60% | | 15 | 328.5 | |
| Remoxipride | 96% | 5-6% | 3-6 | 371.27 | |
| Minaprine | | | 2-2.5 | 298.38 | |
| Tamoxifen | | 99% | 5-7 days | 371.5 | 3A, 2C9. 2D6 |
| Metoprolol | 77% | 12% | 3-7 | 652.8 | |
| Timolol | 90% | <10% | 4 | 316.4 | |
| Alprenolol | 20% | 80% | 2-3 | 249.34 | |
| Carvedilol | 25-35% | 95-98% | 6-10 | 406.5 | 2D6, 2C9, 3A4, 2C19, 1A2 |
| Bufuralol | | | | 297.8 | |
| Nebivolol | 12-96% | 98% | 12-19 | 441.9 | |
| Propranolol | 30-70% | 93% | 3-6 | 295.8 | |
| Debrisoquine | | | | 448.5 | |
| Flecainide | 70-95% | 40% | 20 | 474.4 | |
| Propafenone | 3.4-10.6% | >95% | 2-10 | 377.92 | 2D6, 3A4, 1A2 |
| Encainide | 25-90% | 70.5-78% | 11.3 | 352.47 | |
| Mexiletine | 80-90% | 50-70% | 6-17 | 179.259 | 2D6, 1A2 |
| Lidocaine (mainly by 3A4) | 35% | 60-80% | 1.5-2 | 234.34 | 1A2. 3A4, 2D6 |
| Sparteine | | | | 234.38 | |
| Ondansetron | 56% | 70-76% | 3-6.2 | 293.4 | |
| Donepezil | 100% | 96% | 70 | 379.5 | 2D6, 3A4 |
| Phenformin | 40-60% | 12-20% | 4-13 | 205.26 | |
| Tropisetron | 60-100% | 71% | 5.6-8.6 | 284.4 | |
| Amphetamine | 100% | 20% | 11-12.36 | 135.21 | |
| Methoxyamphetamine | | | | 165.232 | |
| Dextromethamphetamine | | | 12 | 149.24 | |

Table of Exemplary Drugs for Assessing Metabolism by CYP2D6.

| DRUG | ORAL BIOAVAILABILITY | PLASMA PROTEIN BINDING | HALF LIFE (hrs) | MOLECULAR WEIGHT | METABOLISM |
|---|---|---|---|---|---|
| Atomoxetine | 63% | 98% | 5.2 | 291.82 | |
| Chlorphenamine | 25-50% | 72% | 20 | 274.8 | |
| Dexfenfluramine | 68% | 36% | 17-20 | 231.257 | |
| Dextromethorphan | 11% | | 1.4-3.9 | 370.33 | 2D6, 3A4, 3A5 |
| Metoclopramide | 80% | 30% | 5-6 | 354.3 | |
| Perhexiline | | | 12-18 | 277.488 | |
| Phenacetin (analgesic) | | | | 179.216 | |
| Promethazine | 88% | 93% | 16-19 | 284.42 | |

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Alfentanil (Alfenta) | | 92% | 1.5 | 452.98 | |
| Alfuzon (Uroxatral) | 49% | 86% | 10 | 425.9 | |
| Almotriptan (Axert) | 70% | 35% | 3.5 | 469.56 | 2D6, MAO |
| Alprazolam (Xanax) | 90% | 80% | 11 | 308.76 | |
| Amiodarone (Cordarone) | 50% | 96% | >9 days | 681.78 | 2C8 |
| Amlodipine (Norvasc) | 64-90% | 93% | 30-60 | 567.1 | |
| Aprepitant (Emend) | 60-65% | 95% | 9-13 | 534.4 | 1A2, 2C19, 2C9 |
| Atazanavir (Reyataz) | 60-68% | 86% | 7 | 704.9 | |
| Atorvastatin (Lipitor) | 14% | 98% | 7-14 | 558.6 | |
| Bepridil (Vascor) | 60% | 99-100% | 42 | 366.5 | |
| Bexarotene (Targretin) | | 99% | 7 | 348.5 | |
| Bosentan (Tracleer) | 50% | 98% | 5 | 551.6 | 2C9 |
| Bromocriptine (Parlodel) | 65-95% | 90-96% | 6-20 | 654.6 | |
| Budesonide (Entocort) | 9-21% | 85-90% | 2-3.6 | 430.5 | |
| Buprenorphine (Subutex) | 46-65% | 96% | 24-48 | 467.6 | |
| Bupropion (Zyban, Wellbutrin, Voxra) | | 84% | 19-21.3 | 239.7 | 2B6 |
| Carbamazepine (eg, Tegretol) | 89% | 76% | 12-17 | 236.3 | |
| Cevimeline (Evoxac) | | <20% | 4-6 | 199.3 | 2D6, 3A3 |
| Cilostazol (Pletal) | 87-100% | 95-98% | 11-13 | 369.5 | 2C19 |
| Cisapride (Propulsid) | 35-65% | 98% | 6-12 | 465.9 | |
| Clarithromycin (Biaxin) | 55% | Low | 4 | 747.9 | |
| Clonazepam (Klonopin) | 90% | 85% | 30-40 | 315.7 | |
| Clopidogrel (Plavix) | >50% | 94-98% | 6 | 321.8 | 2C19, 3A, 2B6, 1A2 |
| Colchicine | 45% | 39% | 26.6-31.2 | 399.4 | |
| Cyclophosphamide (Cytoxan) | >75% | >60% | 3-12 | 261.1 | |
| Cyclosporine (Neoral) | 30% | 90% | 19 | 1202.6 | |
| Dapsone (Avlosulfon) | 86-104% | 70-90% | 10-50 | 248 | |
| Darunavir (Prezista) | 37% | 95% | 15 | 393.73 | |

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Dasatinib (Sprycel) | | 96% | 3-5 | 488.01 | |
| Delavirdine (Rescriptor) | 85% | 98% | 5.8 | 552.68 | 3A, 2D6 |
| Dexamethasone (Decadron) | 86.10% | 77% | 1.88-2.23 | 392.47 | |
| Dihydroergotamine | <32% | 93% | 9-10 | 679.8 | |
| Diltiazem (Cardizem) | >40% | 70-80% | 3-6 | 450.99 | |
| Disopyramide (Norpace) | 80% | 50-65% | 6.7 | 437.47 | |
| Docetaxel (Taxotere) | 8% | 94-97% | 11.1 | 861.9 | |
| Donepezil (Aricept) | 100% | 96% | 70 | 379.5 | 3A4, 2D6 |
| Doxorubicin (Adriamycin) | 5% | 74-76% | 20-48 | 579.99 | |
| Droperidol | | | 2 | 379.43 | |
| Dutasteride (Avodart) | 60% | 99% | 5 weeks | 528.5 | |
| Ebastine (Kestine) | "High" | 98% | 24.8 | 469.658 | |
| Efavirenz (Sustiva) | 40-45% | 99.5-99.75% | 40-55 | 315.675 | 3A, 2B6 |
| Eletriptan (Relpax) | 50% | 85% | 4 | 463.4 | |
| Eplerenone (Inspra) | 69% | 50% | 3-6 | 414.5 | |
| Ergotamine (Ergomar) | <5% | | 1.5-2.5 | 581.66 | |
| Erlotinib (Tarceva) | 60% | 93% | 36.2 | 393.436 | 3A4, 1A2 |
| Erythromycin | 30-65% | 90% | 1-1.5 | 744.94 | |
| Estazolam (ProSom) | 93% | 93% | 10-24 | 294.74 | |
| Eszopiclone (Lunesta) | | 52-59% | 6 | 388.808 | 3A4, 2E1 |
| Ethinyl Estradiol | 38-48% | 97-98% | 7-36 | 296.403 | |
| Ethosuximide (Zarontin) | 93% | | 25-60 | 141.168 | 3A4, 2E1 |
| Etoposide (Vepesid) | 50% | 97% | 7 | 588.57 | |
| Exemestane (Aromasin) | 42% | 90% | 24 | 296.41 | |
| Felodipine (Plendil) | 13-20% | 99% | 26.7-33.2 | 384.259 | |
| Fentanyl (Sublimaze) | 76-92% | 80-86% | 3-27 | 336.5 | |
| Finasteride (Proscar) | 65% | 90% | 4.5 | 372.55 | |
| Flurazepam (Dalmane) | 83% | 97.2% | 2.3 | 387.9 | |
| Fosamprenavir (Lexiva) | | 90% | 7.7 | 585.608 | |
| Galantamine (Reminyl) | 90% | 18% | 7 | 368.27 | 3A4, 2D6 |
| Gefitinib (Iressa) | 60% | 90% | 48 | 446.9 | 3A4, 2D6 |
| Granisetron (Kytril) | 60% | 65% | 3-24 | 312.4 | 1A1, 3A4 |
| Halofantrine (Halfan) | | 60-70% | 6-10 days | 500.423 | |
| Ifosfamide (Ifex) | 92-100% | 20% | 7 | 261.1 | 3A, 2B1, 2B6 |
| Imatinib (Gleevec) | 98% | 95% | 18 | 589.7 | |
| Indinavir (Crixivan) | 30% | 60% | 1.8 | 711.88 | |
| Irinotecan (Camptosar) | | 30-68% | 6-12 | 677.19 | |
| Isradipine (DynaCirc) | IR: 90-95% CR: 15-24% | 95% | 8 | 371.39 | |

-continued

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Itraconazole (Sporanox) | 55% | 99.8% | 35-64 | 705.64 | |
| Ixabepilone (Ixempra) | | 67-77% | 52 | 506.7 | |
| Ketoconazole (Nizoral) | 75% | 99% | 2-8 | 531.43 | |
| Lapatinib (Tykerb) | | >99% | 24 | 581.1 | 3A4, 3A5 |
| Levomethadyl (Orlaam) | | 80% | 35-60 | 353.5 | |
| Loperamide (Imodium) | 0.30% | 97% | 9-14 | 477 | |
| Lopinavir (Kaletra) | | 98-99% | 5-6 | 628.8 | |
| Loratadine (Claritin) | 100% | 97% | 8 | 382.9 | 2D6, 3A4 |
| Lovastatin (Mevacor) | 5% | >95% | 2-5 | 404.5 | 3A, 2C8 |
| Maraviroc (Selzentry) | 23-33% | 76% | 14-18 | 513.67 | |
| Mefloquine (Lariam) | 85% | 98% | 3 weeks | 414.78 | |
| Methylprednisolone | | 78% | 2-3 | 374.5 | |
| Midazolam (Versed) | PO: 36% | 97% | 3-6 | 362.25 | |
| Mifepristone (Mifeprex) | 69% | 99.2% | 20-85 | 429.6 | |
| Modafinil (Provigil) | | 60% | 7.5-15 | 273.35 | |
| Nefazodone | 20% | >99% | 2-4 | 506.5 | |
| Nevirapine (Viramune) | 80-94% | 60% | 25-45 | 266.3 | 3A4, 2B6 |
| Nicardipine (Cardene) | 35% | >95% | 8.6-14.4 | 515.99 | 3A4, 2C8, 2D6 |
| Nifedipine (Adalat) | 45-56% | 92-98% | 2 | 346.3 | |
| Nimodipine (Nimotop) | 13% | >95% | 8-9 | 418.4 | |
| Nisoldipine (Sular) | 5% | 99% | 13.7 | 388.4 | |
| Nitrendipine (Baypress) | 23% | 97-99% | 2-24 | 360.4 | |
| Oxybutynin (Difropan) | | 91-93% | 7-30 | 357.5 | |
| Oxycodone (Percodan) | 60-87% | 45% | 5.6 | 315.37 | 3A4, 2D6 |
| Paclitaxel (Taxol) | 6.50% | 89-98% | 13.1-57.7 | 853.9 | 2C8, 3A4 |
| Paricalcitol (Zemplar) | 72% | 99.8% | 5-7 | 416.6 | |
| Pimozide (Orap) | 50% | | 55 | 461.56 | 3A4, 1A2, 2D6 |
| Pioglitazone | 50% | >99% | 3-7 | 392.9 | 3A4, 2C8 |
| Praziquantel (Biltricide) | 80% | 80% | 0.8-3 | 312.4 | |
| Prednisolone | 77.6-84.5% | 70-90% | 2-4 | 360.4 | |
| Prednisone | 92% | 70% | 2-3 | 358.43 | |
| Propoxyphene (Darvon) | 40% | 78% | 6-12 | 339.5 | |
| Quazepam (Doral) | 29-35% | >95% | 25-41 | 386.8 | |
| Quetiapine (Seroquel) | 100% | 83% | 6-7 | 883.1 | |
| Quinacrine | | 80-90% | 5 days | 399.96 | |
| Quinidine | 70-80% | 50-88% | 6-8 | 324.43 | |
| Quinine | 76-88% | 69-92% | 9.7-20 | 782.96 | |
| Ranolazine (Ranexa) | 55% | 62% | 7-8.9 | 427.54 | 3A, 2D6 |
| Repaglinide (Prandin) | 55% | >98% | 1 | 452.6 | 3A4, 2C8 |
| Rifabutin (Rimactane) | 53% | 85% | 36-45 | 847.02 | |

Table of Exemplary Drugs for Assessing Metabolism by CYP3A4.

| DRUG | ORAL BIOAVAILABILITY | PLASMA PROTEIN BINDING | HALF-LIFE (hrs) | MOLECULAR WEIGHT | METABOLISM |
|---|---|---|---|---|---|
| Ritonavir (Norvir) | | 98-99% | 3-5 | 720.95 | 3A4, 2D6 |
| Saquinavir (Invirase) | | 98% | 13 | 670.86 | |
| Sibutramine (Meridin) | 77% | 97% | 1.1 | 334.33 | |
| Sildenafil (Viagra) | 41% | 96% | 4 | 666.7 | 3A4, 2C9 |
| Simvastatin (Zocor) | <5% | 95% | 2.8-3.26 | 418.57 | |
| Sirolimus (Rapamune) | 14-27% | 92% | 61.3-72.3 | 914.2 | |
| Solifenacin (Vesicare) | 90% | 98% | 45-68 | 362.5 | |
| Sufentanil (Sufenta) | | 93% | 2.5 | 578.68 | |
| Sunitinib (Sutent) | | 95% | 40-60 | 532.6 | |
| Tacrolimus (Prograf) | 17-31% | 99% | 8.7-37.9 | 822.03 | |
| Tadalafil (Cialis) | | 94% | 15-35 | 389.41 | |
| Tamoxifen (Nolvadex) | | 99% | 5-7 days | 371.5 | 3A4, 2C9, 2D6 |
| Tamsulosin (Flomax) | >90 | 94-99% | 9-15 | 444.98 | 3A4, 2D6 |
| Teniposide (Vumon) | | >99% | 5 | 656.7 | |
| Testosterone | Varies | 98% | varies | 288.4 | |
| Tiagabine (Gabimil) | 90% | 96% | 7-9 | 412 | 3A, 1A2, 2D6, 2C19 |
| Tinidazole (Tindamax) | 100% | 12% | 11.1-14.7 | 247.3 | |
| Tipranavir (Aptivus) | 30?% | 99.9% | 5.5-6 | 602.7 | |
| Topiramate (Topamax) | 80% | 15-41% | 21 | 339.36 | |
| Triazolam (Halcion) | | 89-94% | 2.3 | 343.21 | |
| Vardenafil (Levitra) | 15-44% | 95% | 4-5 | 579.1 | 3A4, 3A5, 2C |
| Verapamil (Calan) | 13-65% | 86-94% | 4-12 | 491.1 | 3A4, 1A2, 2C8, 2C9, 2C18 |
| Vinblastine (Velbane) | | 98-99.7% | 24.8 | 909.06 | |
| Vincristine (Oncovin) | | | 85 | 923.04 | |
| Ziprasidone (Geodon) | 60% | >99% | 7 | 467.42 | 3A4, 1A2 |
| Zolpidem (Ambien) | 70% | 92.5% | 2.5-2.8 | 764.9 | |
| Zonisamide (Zonegran) | | 40-60% | 63 | 212.23 | |
| Zopiclone (Imovane) | 80% | 45% | 3.5-6.5 | 388.8 | |

Table of Exemplary Tyrosine Kinase Inhibitor Substrates for Assessing Metabolism by CYP3A4.

| DRUG | F % | Protein binding % | T½ | MW |
|---|---|---|---|---|
| erlotinib | 59 | 95 | 36.2 | 393.4 |
| gefitinib | 59 | 90 | 6-49 h | 446.9 |
| pazopanib | 14-21 | >99.5 | 30.9-31.9 h | 437.5 |
| sorafenib | 38-49 | 99.5 | 25-48 h | 464.8 |
| sunitinib | 50 | 95 | 40-60 h | 398.5 |

In the disclosed methods, the composition administered to the subject may include a substrate for CYP isoform 1A2 ($SUB_{CYP1A2}$). In some embodiments, the substrate for CYP1A2 ($SUB_{CYP1A2}$) is also a substrate for additional enzymes such as additional CYP isoforms such as isoform 2A6 or other enzymes such as N-acetyl transferases (NATs) and/or xanthine oxidases (XOs). In some embodiments, the substrate for CYP isoform 1A2 is also a substrate for each of CYP1A2, CYP2A6, NAT, and XO. Suitable substrates for CYP1A2 may include but are not limited to caffeine (e.g., where the metabolite ($MET_{CYP1A2}$) is paraxanthine) and theophylline.

In the disclosed methods, the composition administered to the subject may include a substrate for CYP isoform 2C19 ($SUB_{CYP2C19}$). In some embodiments, the substrate for CYP2C19 also is a substrate for additional enzymes such as additional CYP isoforms such as isoform 3A4 ($SUB_{CYP3A4}$). Suitable substrates for CYP2C19 may include but are not limited to omeprazole (e.g., where the metabolite ($MET_{CYP2C19}$) is 5OH-omeprazole), esomeprazole, mephenytoin, clopidogrel, and phenytoin. In some embodiments, the composition administered to the subject includes omeprazole and a basic buffering agent, which may include but is not limited to sodium bicarbonate and/or calcium carbonate.

In the disclosed methods, the composition administered to the subject may include a substrate for CYP isoform 2D6 ($SUB_{CYP2D6}$). Suitable substrates for CYP2D6 may include but are not limited to dextromethorphan (e.g., where the metabolite ($MET_{CYP2D6}$) is dextrorphan), desipramine, and metoprolol.

In the disclosed methods, the composition administered to the subject may include a substrate for CYP isoform 3A4 ($SUB_{CYP3A4}$), for example, wherein a metabolite ($MET_{CYP3A4}$) is subsequently detected in saliva of the subject and any unmetabolized $SUB_{CYP3A4}$. Suitable substrates for CYP3A4 may include but are not limited to eplerenone (e.g., where the metabolite ($MET_{CYP33A4}$) is 6β-hydroxyeplerenone and/or 21-hydroxyeplerenone), midazolam, simvastatin, alfentanil, dextrormethorphan, omeprazole, erythromycin, cortisol, midazolam, quindine, and triazolam.

In the disclosed methods, the composition administered to a subject typically includes $SUB_{CY3A4}$ and optionally may comprise a mixture including $SUB_{CY3A4}$ and further including one or more of $SUB_{CYP1A2}$, $SUB_{CYP2C19}$, and/or $SUB_{CYP2D6}$, and $SUB_{CY3A4}$. In some embodiments of the disclosed methods, the composition administered to the subject further includes a substrate for an enzyme selected from one or more of CYP2C9, and CYP2E1 (i.e., $SUB_{CYP2A9}$ and $SUB_{CYP2E1}$, respectively).

In the disclosed methods, the composition administered to the subject further include may include a substrate for CYP isoform 2C9 ($SUB_{CYP2C9}$), for example, wherein a metabolite ($MET_{CYP2c9}$) is subsequently detected in saliva of the subject and any unmetabolized $SUB_{CYP2C9}$. Suitable substrates for CYP2C9 may include but are not limited to warfarin, tolbutamide, diclofenac, flurbiprofen, celecoxib, lornoxicam, ibuprofen, naproxen, ketoprofen, piroxicam, meloxicam, suprofen, phenytoin, fluvastatin, glipizide, glibenclamide, glimepiride, glyburide, irbesartan, losartan, S-warfarin, sildenafil, terbinafine, amitriptyline, fluoxetine, nateglinide, rosiglitazone, tamoxifen, torasemide, ketamine, THC, JWH-018, AM-2201, and limonene.

In the disclosed methods, the composition administered to the subject further include may include a substrate for CYP isoform 2E1 ($SUB_{CYP2E1}$), for example, wherein a metabolite ($MET_{CYP2E1}$) is subsequently detected in saliva of the subject and any unmetabolized $SUB_{CYP2E1}$. Suitable substrates for CYP2E1 may include but are not limited to chlorzoxazone, desipramine, and metoprolol.

In the disclosed methods, the composition administered to the subject may include a substrate for additional enzymes which are not CYP isoforms. In some embodiments of the disclosed methods a mixture of substrates administered to the subject may include a substrate for an enzyme selected from a group consisting of an N-acetyl transferase (NAT), a methyl transferase, a UDP glucuronosyl transferase (UGT), a sulfo transferases, and an oxidative enzyme, or a combination thereof. In some embodiments of the disclosed methods, a mixture of substrates administered to the subject may include a substrate for an isoform of UDP glucuronosyl transferase (UGT), which may include, but is not limited to a substrate for one or more of UGT1A1, UGT1A4, UGT1A6, UGT1A9, and UGT2B7.

In some embodiments of the disclosed methods, the composition administered to the subject may include as a substrate ketoprofen. The method further may include detecting one or more metabolites selected from beta-estradio-3-glucuronide, trifluoperazine-N-glucuronide, 5-hydroxytryptophol-O-glucuronide, propofol-O-glucuronide, zidovudine-5'-glucuronide, and combinations thereof.

The disclosed methods may include determining a metabolic ratio based on one or more metabolites detected in saliva versus one or more unconverted substrates detected in saliva (e.g., METCYP/SUBCYP detected in saliva after having administered SUBCYP and having waiting for a period of time such as 0.5, 1.0, 1.5, 2.0, 2.5, 3.0, 3.5, 4.0, 4.5, 5.0, 5.5, 6.0, 7.0, 8.0, 9.0, 10.0, 11.0, 12.0, 24.0 hours or more).

The disclosed methods typically include determining a metabolic ratio for $MET_{CYP3A5}$ and unconverted $SUB_{CYP3A5}$ (e.g., 6β-hydroxyeplerenone and/or 21-hydroxyeplerenone versus eplerenone). Optionally, the disclosed methods may include determining a metabolic ratio for one or more of: (i) $MET_{CYP1A2}$ and unconverted $SUB_{CYP1A2}$ (e.g., caffeine versus paraxanthine); (ii) $MET_{CYP2C19}$ and unconverted $SUB_{CYP2C19}$ (e.g.-, omeprazole versus 5OH-omeprazole); (iii) $MET_{CYP2D6}$ and unconverted $SUB_{CYP2D6}$ (e.g., dextromethorphan versus dextrorphan); (iv) $MET_{CYP3A4}$ and unconverted $SUB_{CYP3A4}$; (v) $MET_{CYP2C9}$ and unconverted $SUB_{CYP2C9}$; and/or (vi) $MET_{CYP2E1}$ and unconverted $SUB_{CYP2E1}$.

Also disclosed herein are compositions suitable for use in the disclosed methods. The disclosed compositions typically comprise a substrate for CYP3A5 $SUB_{CYP3A5}$ (e.g., eplerenone). Optionally, the disclosed compositions may comprise one or more additional substrates for one or more additional CYP isoforms (e.g., one or more substrates for one or more of CYP1A2, CYP2C9, CYP2C19, CYP2E1, CYP2D6, and/or CYP3A4). In some embodiments, the compositions comprise a substrate for CYP3A5 ($SUB_{CYP3A5}$), wherein CYP3A4 catalyzes conversion of $SUB_{CYP3A5}$ to a metabolite ($MET_{CYP3A5}$) and optionally the compositions further may comprise one or more of: (i) a substrate for CYP1A2 ($SUB_{CYP1A2}$), wherein CYP1A2 catalyzes conversion of $SUB_{CYP1A}$ to a metabolite ($MET_{CYP1A2}$); (ii) a substrate for CYP2C19 ($SUB_{CYP2C19}$), wherein CYP2C19 catalyzes conversion of $SUB_{2C19}$ to a metabolite ($MET_{CYP2C19}$), (iii) a substrate for CYP2D6 ($SUB_{CYP2D6}$), wherein CYP2D6 catalyzes conversion of $SUB_{CYP2D6}$ to a metabolite ($MET_{CYP2D6}$); and/or (iv) a substrate for CYP3A4 ($SUB_{CYP3A4}$), wherein CYP3A4 catalyzes conversion of $SUB_{CYP3A4}$ to a metabolite ($MET_{CYP3A4}$). Substrates for the disclosed compositions may include one or more "drugs" as known in the art and as provided above in the "Table of Exemplary Drugs."

The disclosed compositions may comprise one or more tablet formulations of $SUB_{CY3A5}$. Optionally, the disclosed composition may comprise one or more substrates selected from $SUB_{CYP1A2}$, $SUB_{CYP2C19}$, $SUB_{CYP2D6}$, and/or $SUB_{CY3A4}$. In some embodiments, the composition includes multiple tablets, for example, one tablet of $SUB_{CY3A5}$ and optionally one table of one or more of $SUB_{CYP1A2}$, $SUB_{CYP2C19}$, $SUB_{CYP2D6}$, and/or $SUB_{CY3A4}$. In other embodiments, the composition administered to the subject may comprise a single tablet formulation, the single table formulation including $SUB_{CY3A5}$ and optionally include one or more of substrates selected from $SUB_{CYP1A2}$, $SUB_{CYP2C19}$, $SUB_{CYP2D6}$, and/or $SUB_{CY3A4}$. Suitable tablet formulations may include immediate release tablet formulations, for example an immediate table release formulation for $SUB_{CYP3A5}$ and optionally an immediate table release formulation for one or more of $SUB_{CYP1A2}$, $SUB_{CYP2C19}$, $SUB_{CYP2D6}$, and/or $SUB_{CYP3A4}$. In some embodiments, the tablet formulations may include a non-substrate coating (e.g., an enteric coating).

The disclosed compositions typically include a substrate for CYP3A5 ($SUB_{CYP3A5}$), such as eplerenone. In some embodiments, a substrate of the composition is a substrate for more than one isoform of CYP (e.g., a substrate for CYP3A5 may additionally be a substrate for CYP3A4 and/or a substrate for CYP3A4 may additional be a substrate for CYP3A5). In other embodiments, a substrate of the composition is a substrate for one isoform of CYP and is not a substrate for another or any other isoform of CYP (e.g., a substrate for CYP3A5 may not be a substrate for CYP3A4 and/or a substrate for CYP3A4 may not be a substrate for CYP3A5).

As such, the disclosed compositions comprise $SUB_C$ and the disclosed compositions optionally may comprise one or more of $SUB_{CYP1A2}$, $SUB_{CYP2C19}$, $SUB_{CYP2D6}$, and/or $SUB_{CYP3A4}$. In some embodiments of the disclosed compositions, $SUB_{CYP3A5}$ may also be a substrate for other CYP isoforms or substrates for other enzymes. For example, $SUB_{CYP3A5}$ also may be a substrate for an enzyme selected from the group consisting of CYP3A4. In some embodiments of the disclosed compositions, $SUB_{CYP1A2}$ may also be a substrate for other CYP isoforms or substrates for other enzymes. For example, $SUB_{CYP1A2}$ also may be a substrate for an enzyme selected from the group consisting of CYP2A6, NAT2, XO, and combinations thereof. In some embodiments, of the disclosed compositions, $SUB_{CYP2C19}$ may also be a substrate for other CYP isoforms or substrates for other enzymes. For example $SUB_{CYP2C19}$ may also be a substrate for CYP3A4.

The disclosed compositions typically include a substrate for CYP3A5 ($SUB_{CYP3A5}$). Suitable substrates for CYP3A5 ($SUB_{CYP3A5}$) may include eplerenone. Other suitable substrates for CYP3A5 ($SUB_{CYP3A5}$) may include alprazolam (α-hydroxylation), cortisol, alfentanil, midazolam, tacrolimus, and triazolam, and vincristine.

The disclosed compositions optionally may include additional substrates for additional CYP450 enzymes. Suitable additional substrates for the disclosed composition may include, but are not limited to, one or more of: (i) $SUB_{CYP1A2}$ selected from caffeine and theophylline; (ii) $SUB_{CYP2C19}$ selected from omeprazole, esomeprazole, mephenytoin, clopidogrel, and phenytoin; (iii) $SUB_{CYP2D6}$ selected from dextromethorphan, desipramine, and metoprolol; (iv) $SUB_{CYP3A4}$ selected from eplerenone, midazolam, simvastatin, alfentanil, dextrormethorphan, omeprazole, erythromycin, cortisol, midazolam, quindine, and triazolam. In particular, additional suitable substrates for the disclosed compositions may include one or more of caffeine, omeprazole, and dextromethorphan, and optionally a basic buffering agent, which may include but is not limited to sodium bicarbonate and/or calcium carbonate; and/or Optionally, the disclosed mixtures may include a substrate for one or more of CYP2C9 and CYP2E1.

Optionally, the disclosed compositions further may comprise a substrate for a non-CYP450 enzyme selected from an N-acetyl transferase (NAT), a methyl transferase, a UDP glucuronosyl transferase (UGT), a sulfo transferases, and an oxidative enzyme, or a combination thereof. Optionally, the compositions further comprises a substrate for an isoform of UDP glucuronosyl transferase (UGT) selected from the group consisting of UGT1A1, UGT1A4, UGT1A6, UGT1A9, and UGT2B7. Optionally, the disclosed compositions further may comprise ketoprofen.

The substrates utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, an immediate release form. In some embodiment, the substrates may be formulated in the same dosage form (e.g., all tablet form). In other embodiments, the substrates may be formulated in different dosage forms (e.g., some in tablet form others in powder form).

In some embodiments, the disclosed composition may include a buffer. For example, the composition may include a basic buffering agent, which may include but is not limited to sodium bicarbonate and/or calcium carbonate.

In some embodiments, the disclosed composition may have s a basic pH when the composition is dissolved in water. For example, the composition may have a pH greater than about 7.5, 8.0, 8.5, or 9.0 when dissolved in water.

The substrates utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The substrates utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

The substrates utilized in the methods disclosed herein may be formulated as a pharmaceutical composition for delivery via any suitable route. For example, the pharmaceutical composition may be administered via oral routes, sublingual routes, or buccal routes. Examples of pharmaceutical compositions for administration include capsules, syrups, concentrates, powders and granules. Suitable capsules may include hard gelatin capsules or softgels (aka soft gelatin capsules). The substrates utilized in the methods disclosed herein also may be formulated as a pharmaceutical composition for delivery via parenteral administration, such as intravenous delivery, subcutaneious delivery, and/or intramuscular delivery.

The substrates utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Also disclosed herein are kits. The disclosed kits may be utilized for testing metabolic activity in a subject and/or determining a phenotype of a subject. For example, the kits may be utilized for testing metabolic activity of one or more CYP450 isoforms and/or determining a phenotype of a subject in regarding to the activity of one or more CYP450 isoforms. The disclosed kits may include as a component any of the compositions and/or substrates disclosed herein. In some embodiments, the disclosed kits include one or more additional components selected from the group consisting of: (i) containers (e.g., salivettes) for collecting and transporting saliva samples; (ii) components and/or reagents for performing a UPLC-MS/MS assay; and/or (iii) components for generating a report of the results of the UPLC-MS/MS assay.

EXAMPLES

The following Examples are illustrative and are not intended to limit the scope of the claimed subject matter.

Example 1

Eplerenone in Saliva as a CYP3A4/5 Metabolic Phenotyping Probe

Abstract

The field of pharmacogenetics began with the observation that some individuals possessed extreme differences in their ability to metabolize certain drugs. Advances in genetics allowed for identification of polymorphisms in drug metabolizing enzymes, which had a significant impact on drug elimination. The medical literature contains many examples of the impact of genetic polymorphisms on drug metabolizing enzyme activity. However, genetics do not account for the significant impact of post transcriptional/translational regulation and environmental exposures on enzyme activity. In addition, the impact on phenotype is unknown for many variants. To address these discrepancies we have developed a CYP3A4/5 metabolic phenotyping tool, which utilizes saliva sampling as a non-invasive, fast, and easy metabolic phenotyping matrix.

Utilizing SimCYP, we were able to create a model of eplerenone as a substrate probe for CYP3A4/5 in saliva. The SimCYP model shows good agreement with clinical data. SimCYP models allowed optimization of the timing of metabolic ratio measurements and gave excellent estimates of population level variability. Using SimCYP we were able to validate eplerenone metabolic phenotyping as a rapid, simple, and robust tool to determine CYP3A4 and CYP3A4/5 enzyme activity on an individual and population level. Future work will be aimed at identifying the relationship between eplerenone metabolic ratio, dosing of other CYP3A4/5 substrates, and clinical outcomes.

Introduction

Eplerenone is an aldosterone antagonist with enhanced aldosterone receptor specificity but similar effects as the potassium sparing diuretic spironolactone. Eplerenone is metabolized via hepatic CYP3A4 and to a lesser extent through CYP3A5. CYP3A4 preferentially generates 6β-hydroxy eplerenone over 21-hydroxy eplerenone while CYP3A5 generates 6β-hydroxy eplerenone and 21-hydroxy eplerenone at similar rates. The specific metabolism of eplerenone to its 6β-hydroxy metabolite via CYP3A4 and concomitant formation of the 21-hydroxy metabolite by CYP3A4 and CYP3A5 make it an attractive potential substrate probe. Currently, testosterone and midazolam are the most commonly utilized probe substrates for CYP3A4 activity (Patki, Von Moltke et al. 2003). However, both have significant limitations for use as in vivo substrate probes. Testosterone exerts potent hormonal effects if given exogenously, and endogenous secretion is very low in women and varies throughout the day (Mezzullo, Fazzini et al. 2017). Oral midazolam causes sedation, and metabolic ratio measurements do not correlate well with midazolam clearance via CYP3A4 (Lee, Bertino et al. 2006, Penzak, Busse et al. 2008). To overcome these difficulties we investigated the use of salivary eplerenone metabolic ratios as probes of CYP3A4/5 activity. We then utilized SimCYP to externally validate our results.

Materials and Methods

Human Subject. Twelve healthy volunteers aged 22-62 years old were screened for "healthy" status through a brief questionnaire and a physician's physical assessment. After screening, subjects fasted overnight and received 50 mg eplerenone tablets in the morning. Approximately 1 ml of saliva was collected in a microcentrifuge tube at 0.5, 1, 2, 3, 4, 5, and 6 hours. After collection, samples were stored at −20° C. and transferred to a −80° C. freezer until the time of analysis.

Saliva Extraction. Saliva samples were preserved in a −80° C. freezer until ready for extraction. Samples were then vortexed and centrifuged at 13,100 rpm for 10 min until mucous was precipitated. Saliva was decanted into a fresh microcentrifuge tube and 250 mcl of saliva was removed and added to a 3 kD centrifugal filter. To the filter were also added 10 mcl diazepam standard (4 mg/ml and 240 mcl methanol (at −20° C. to −80° C.). Samples were vortexed and centrifuged at 13,100 rpm for 20-30 min. Filtrate was transferred to an HPLC vial and either run through the mass spectrometer or stored back in the −80° C. freezer.

UHPLC MS/MS Methods. Chemical analysis was performed by a Sciex 4000 Qtrap and Dionex RSLC 3000 UHPLC. Solution A consisted of water with 5% MeOH, 0.05% acetic acid, and solution B contained 35% acetonitrile, 65% MeOH, with 0.05% acetic acid. The Acquity UHPLC HSS T3 1.8 mcm, 2.1*50 mm column was equilibrated with 50% B for 0.2 min then changed to 95% B 0.35 minutes after injection and ramped from 95% B at 0.35 min to 100% B at 2.75 min, which was held for 0.75 minutes.

Using APCI positive mode, Curtain gas 30, Source Temperature 400° C., Source gas 1 80 psi, gas 2 60 psi, collision gas high, ion spray voltage 5500 V. Analyte MRMs with DP and CE were: eplerenone (415/163 DP 60, CE 30, CXP 10), 63-hydroxy Eplerenone (431/211 DP 60, CE 20, CXP 10), 21-hydroxy eplerenone (431/163 DP 60, CE 20, CXP 10), and diazepam (285/193 DP 90, CE 45, CXP 13).

SimCYP Modeling. SimCYP models were created using eplerenone and metabolite physicochemical and pharmacokinetic properties reported in the literature. SimCYP parameter estimation (P.E.) was utilized to fit pharmacokinetic properties for metabolites when literature values were not available. The appendix lists P.E. results. Preloaded SimCYP version 15 models were used to gather AUC and $CL_{int}$ for alprazolam, midazolam, nifedipine, triazolam, cyclosporine, quinidine, saquanavir, sildenafil, simvastatin, and zolpidem.

Statistics. Statistical results were obtained from IBM SPSS version 24. Histograms of metabolic ratios were generated using Graphpad Prism 6.

Results

SimCYP models were built using data from Cook et al., in vitro data from McGraw et al., and saliva data from the subjects in this study (Cook, Berry et al. 2003). Table 1 shows the parameters for eplerenone and its major metabolites included in the SimCYP model.

and its metabolites versus mean saliva data concentration versus time profiles. Actual data falls close to the projected data that simulates an average person in the 50th percentile of metabolic activity for this probe. The good agreement between modeled unbound plasma concentrations and saliva data indicate that saliva pharmacokinetics closely mimic plasma kinetics. Comparison between unbound plasma concentations of metabolites was not necessary since the $f_u$ was assumed to have a value of 1.

TABLE 1

Eplerenone and Metabolites SimCYP Model Parameters

| Parameter | EP | 6OH-EP | 21OH-EP |
|---|---|---|---|
| Physical Chemical and Blood Binding | | | |
| Molecular Weight (g/mol) | 414.49 | 430.49 | 430.49 |
| LogP | 1.02 | 0.28 | 0.37 |
| Compound Type | Neutral | Neutral | Neutral |
| Blood/plasma ratio | 0.74 | 1 | 1 |
| fu | 0.5 | 1 | 1 |
| Absorption | | | |
| Model Type | 1st order | | |
| fa, fuGut | 0.983, 1 | | |
| ka (h$^{-1}$) | 1.647 | | |
| Lag time | 0.25 | | |
| Qgut (L/h) | 12.32 Predicted | | |
| Permeability ($P_{eff}$man 10$^{-4}$ cm/s) | 4 Predicted | | |
| Permeability model | Caco-2 (24* 10$^{-6}$ cm/s) | | |
| Distribution | | | |
| Model Type | Minimal | Minimal | Minimal |
| Vss (L/kg) | 0.47 Predicted Method 2 | 0.51 | 0.53 |
| Elimination | | | |
| Model Type | Enzyme kinetics | In Vivo | In Vivo |
| CL PO | | CL 24.3 (9.6) | CL 17.8 (14) |
| Path, Enzyme, Vmax, Km, fu$_{mic}$ | 6OH - CYP3A4, 973, 217, 0.85 | | |
| Path, Enzyme, Vmax, Km, fu$_{mic}$ | 6OH - CYP3A5, 168, 113, 0.85 | | |
| Path, Enzyme, Vmax, Km, fu$_{mic}$ | 21OH - CYP3A4 0.286, 211, 0.68 | | |
| Path, Enzyme, Vmax, Km, fu$_{mic}$ | 21OH - CYP3A5 165, 88, 0.80 | | |

The timepoint of 4 hours was chosen as the optimal time to measure metabolic ratio based on SimCYP modeling correlations between log Metabolic Ratio (MR), log unbound AUC (AUC$_u$), and log hepatic intrinsic clearance (CL$_{int}$). (See Table 2).

Table 3 compares the statistical parameters obtained from clinical research subjects versus the virtual subjects generated by SimCYP. Reports of variability of CYP3A4/5 activity differ significantly in the literature (McGraw 2014). Subject metabolic ratios of eplerenone's 6β-hydroxy

TABLE 2

Spearman Correlations between log Eplerenone, log eplerenone MRs, log CL, and log AUC$_u$

| Spearman correlation | Log Eplerenone | | 6OH-Eplerenone log MR | | 21OH-Eplerenone log MR | |
|---|---|---|---|---|---|---|
| Hour | log AUC$_u$ | log CL$_{int}$ | log AUC$_u$ | log CL$_{int}$ | log AUC$_u$ | log CL$_{int}$ |
| 1 | 0.71 | −0.68 | 0.73 | −0.74 | 0.69 | −0.69 |
| 2 | 0.92 | −0.89 | 0.85 | −0.86 | 0.79 | −0.80 |
| 3 | 0.98 | −0.97 | 0.90 | −0.91 | 0.86 | −0.87 |
| 4 | 0.99 | −0.98 | 0.92 | −0.93 | 0.89 | −0.90 |
| 5 | 0.99 | −0.98 | 0.92 | −0.93 | 0.90 | −0.92 |
| 6 | 0.98 | −0.98 | 0.90 | −0.91 | 0.90 | −0.91 |

Figure 3:
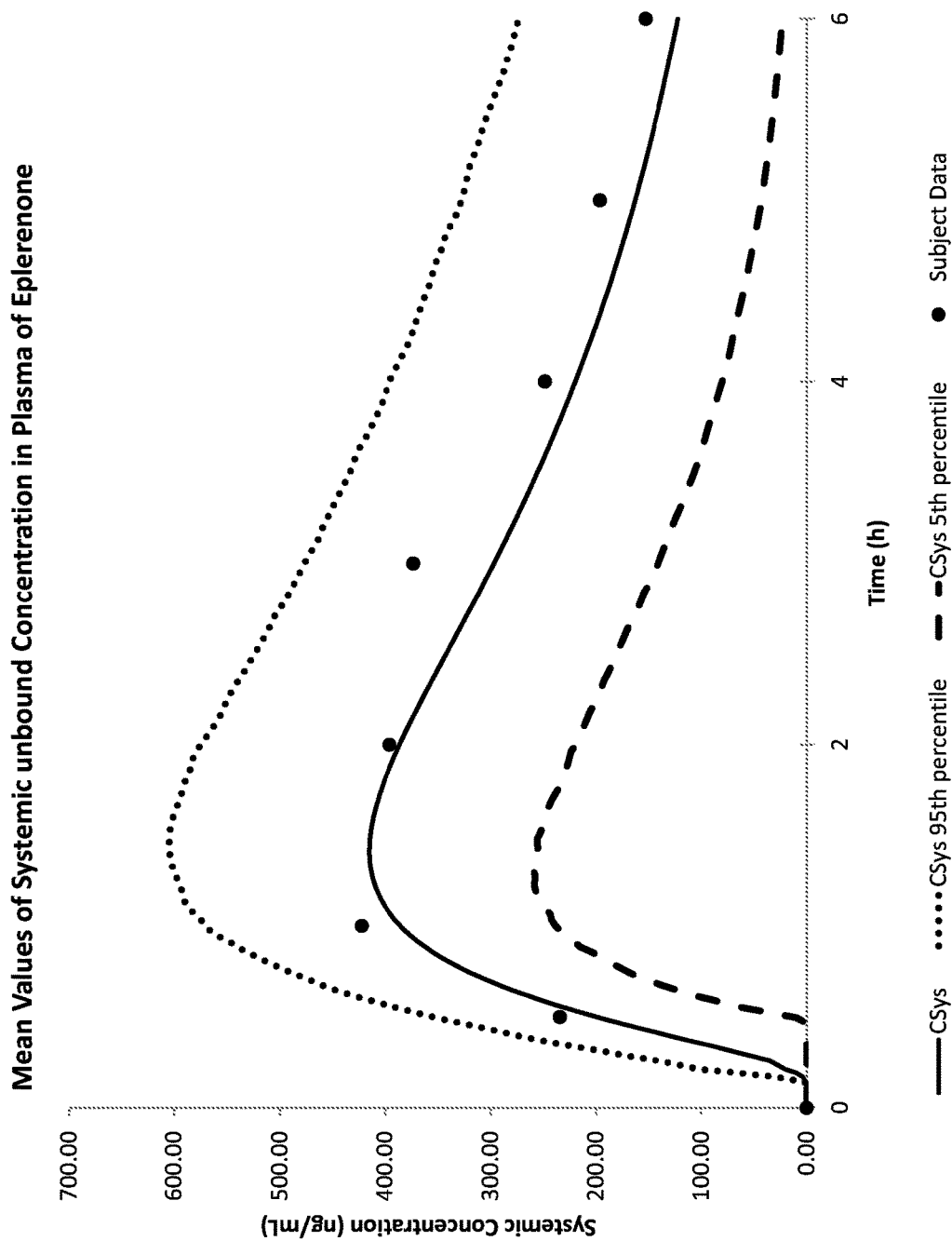
FIG. 3 shows unbound concentration of eplerenone in plasma over time.

FIG. 3 shows an overlay of SimCYP modeled average concentration versus time profiles for unbound eplerenone metabolite, and 21OH metabolite showed an approximate 5 fold variability. This is in-line with previous estimates of constitutive CYP3A4 activity (Galetin, Brown et al. 2004, Wilkinson 2005). However, when the sample population was expanded using SimCYP we observed a much larger increase in variability. The 4 hr eplerenone concentrations showed approximately 50 fold variability which is in-line with other estimates of CYP3A4 variability (Ingelman-Sundberg 2004). The 21OH MRs showed over 200 fold variability for the 21OH metabolite which is approaching the variability which has been previously attributed to factors such as illness and/or inhibition and induction interactions (McGraw 2014).

low unimodal distributions. Therefore, widespread categorical nomenclature such as poor metabolizer, rapid metabolizer, etc . . . is not available. To address population variability in metabolic phenotype, phenotypic metrics were categorized using SPSS statistical software. Genetic predictions of metabolic phenotype lend themselves to categorical interpretation since allele presence or absence is a dichotomous variable. We compared the ability of the phenotypic metrics to characterize AUC for two prototypical substrates

TABLE 3

Four hour Eplerenone and Metabolic Ratios in Research Subjects versus Virtual Subjects

|  | Research Subjects | | | Virtual Subjects | | |
| --- | --- | --- | --- | --- | --- | --- |
|  | EP | 6OH MR | 21OH MR | EPu | 6OH MR | 21OH MR |
| AVG | 169.0 | 0.9 | 2.6 | 217.9 | 1.3 | 3.2 |
| % SD | 70.2 | 53.3 | 36.9 | 47.6 | 65.4 | 75 |
| Min | 23.4 | 0.3 | 0.9 | 13.8 | 0.2 | 0.1 |
| Max | 322.0 | 1.8 | 4.5 | 718.3 | 7.3 | 20.6 |
| Max/Min | 13.8 | 5.5 | 4.9 | 52.1 | 36.5 | 206 |

Using SimCYP, we were then able to validate our eplerenone model and phenotypic metrics. We tested whether the metrics could predict AUC for other CYP3A4/5 substrates bedsides eplerenone. Table 4. shows the Spearman correlations between the eplerenone metabolic phenotype metrics (log EP 4 hr, log 6OH MR, and log 21OH MR) and SimCYP derived CYP3A substrate PK parameters (log AUC and log $CL_{int}$). The right of the table describes the percent contribution of CYP3A to the metabolism of each substrate, the relative contribution of CYP3A5, and whether or not the contribution of CYP3A5 to clearance was included in the SimCYP model.

midazolam and nifedipine. Optimal categories for each of the EP phenotypic metrics (logEP 4 hr, log6OH MR, and log21OH MR) were created to capture the relationship between categorical phenotype and log substrate AUC. A categorical approach to phenotype allows comparison to other pharmacogenetic studies in which phenotype is reported as a categorical variable. We optimized the bins with respect to 20 bins of Midazolam AUC (5% for each bin) using SPSS's "optimal binning" function. We optimized the bins with respect to midazolam AUC instead of eplerenone AUC to avoid biasing the bins. The use of midazolam for

TABLE 4

Correlation between Eplerenone Metabolic Phenotype Metrics and SimCYP CYP3A Substrate PK Parameters

| Spearman's rho | Correlation with log AUC | | | Correlation with log CLint | | | All CYP3A | CYP3A5 | CYP3A5 in SimCYP |
| --- | --- | --- | --- | --- | --- | --- | --- | --- | --- |
| Substrate | logEp4hr | log6OHMR | log21OHMR | logEp4hr | log6OHMR | log21OHMR | (% Metabolism) | (% Metabolism) | Model |
| Alprazolam | 0.81 | 0.72 | 0.70 | −0.98 | −0.92 | −0.89 | 62 | <10 | Y |
| Nifedipine | 0.77 | 0.76 | 0.66 | −0.89 | −0.88 | −0.75 | 95 | 14 | Y |
| Triazolam | 0.85 | 0.77 | 0.82 | −0.97 | −0.90 | −0.92 | 92 | 25 | Y |
| Midazolam | 0.83 | 0.74 | 0.82 | −0.95 | −0.87 | −0.92 | 92 | 43 | Y |
| Cyclosporin | 0.85 | 0.76 | 0.83 | −0.95 | −0.88 | −0.92 | NR | 64 | Y |
| Quinidine | 0.78 | 0.76 | 0.64 | −0.87 | −0.87 | −0.73 | 93 | 43 | N |
| Saquinavir | 0.72 | 0.71 | 0.61 | −0.88 | −0.87 | −0.73 | 99 | 11 | N |
| Sildenafil | 0.77 | 0.75 | 0.65 | −0.86 | −0.85 | −0.71 | NR | NR | N |
| Simvastatin | 0.59 | 0.58 | 0.50 | −0.87 | −0.85 | −0.70 | 92 | 17 | N |
| Zolpidem | 0.58 | 0.54 | 0.48 | −0.66 | −0.63 | −0.54 | NR | NR | N |

The purpose of utilizing eplerenone as a metabolic phenotyping probe is to accurately predict AUC for any CYP3A4/5 substrate. Table 4 depicts correlations between eplerenone phenotypic metrics and AUC for a number of CYP3A4/5 substrates. CYP 3A4 and CYP3A5 activity fol- AUC categories and eplerenone for phenotypic metrics should enhance the ability of the phenotypic metrics to predict AUC of other CYP3A substrates besides eplerenone. The optimized bins for each phenotypic metric (log EP 4 hr, log MR21OH, and log MR 6OH) are listed in Table 5.

TABLE 5

SPSS optimal binning segments for midazolam AUC with 'N' number of virtual subjects

|  | Bin 1 | N | Bin 2 | N | Bin 3 | N | Bin 4 | N | Bin 5 | N | Bin 6 | N |
|---|---|---|---|---|---|---|---|---|---|---|---|---|
| Log EP 4 HR | <88 | 49 | 1.88≤2.07 | 104 | 2.07≤2.24 | 213 | 2.24≤2.37 | 239 | 2.37≤2.52 | 253 | ≥2.52 | 142 |
| Log MR21OH | <−0.17 | 62 | −0.17≤0.1 | 118 | 0.1≤0.43 | 331 | 0.43≤0.72 | 335 | ≥0.72 | 154 | | |
| Log MR 6OH | <−0.47 | 36 | −0.47≤−0.13 | 233 | −0.13≤0.13 | 362 | 0.13≤0.35 | 252 | ≥0.35 | 116 | | |

Discussion

Midazolam is the most commonly used probe to assess CYP3A4 activity reported in the literature. However, single midazolam samples or midazolam/1'-hydroxy-midazolam metabolic ratios have questionable validity and utility as CYP3A phenotypic metrics (Penzak, Busse et al. 2008). Determination of midazolam AUC is considered the best approach to CYP3A phenotyping, yet it is problematic since AUC determination requires several blood draws (Mueller and Drewelow 2013). A recent review calls for a CYP3A probe that is cheap, easy, supports clinical dosing decisions, and improves patient outcomes (Hohmann, Haefeli et al. 2016). Our results indicate that eplerenone phenotyping may provide an ideal solution to the CYP3A phenotyping problem. Eplerenone has no sedative effects, saliva samples are more conveniently obtained from patients than plasma, and the boxplots indicate categorical designations of CYP3A4/5 metabolic phenotype can be readily assigned.

Figure 2A:
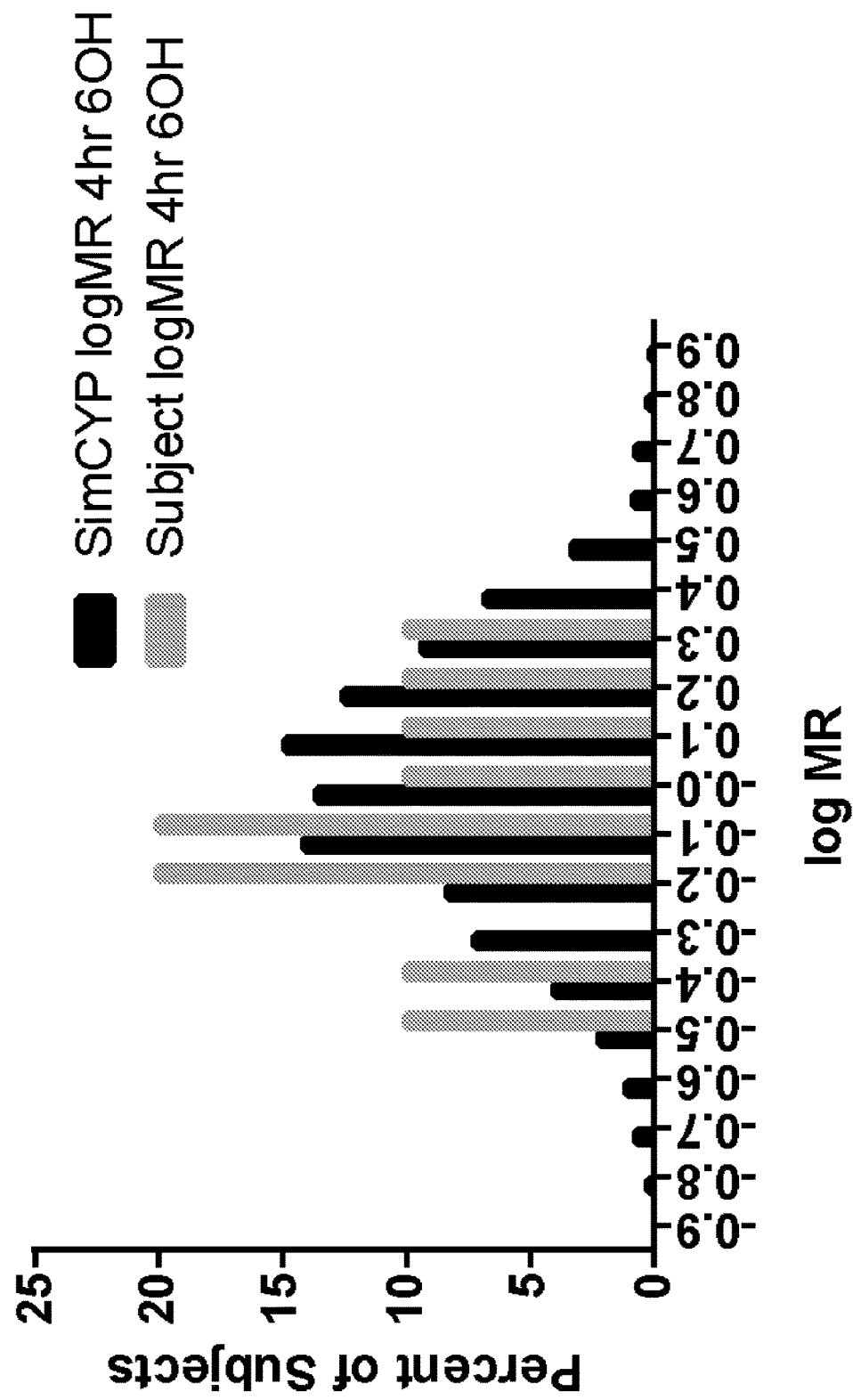
FIGS. 2A and 2B show histograms of metabolic ratios generated from SimCYP models overlaid with clinical data (FIG. 2A—6β-hydroxyeplerenone/eplerenone, FIG. 2B—21-hydroxyeplerenone/eplerenone). There is good agreement between modeled data and clinical data regarding centrality of the histograms and relative spread. The bar height of the clinical data and histograms differ expectedly due to the relatively sparse number of clinical subjects versus virtual subjects.
Figure 2B:
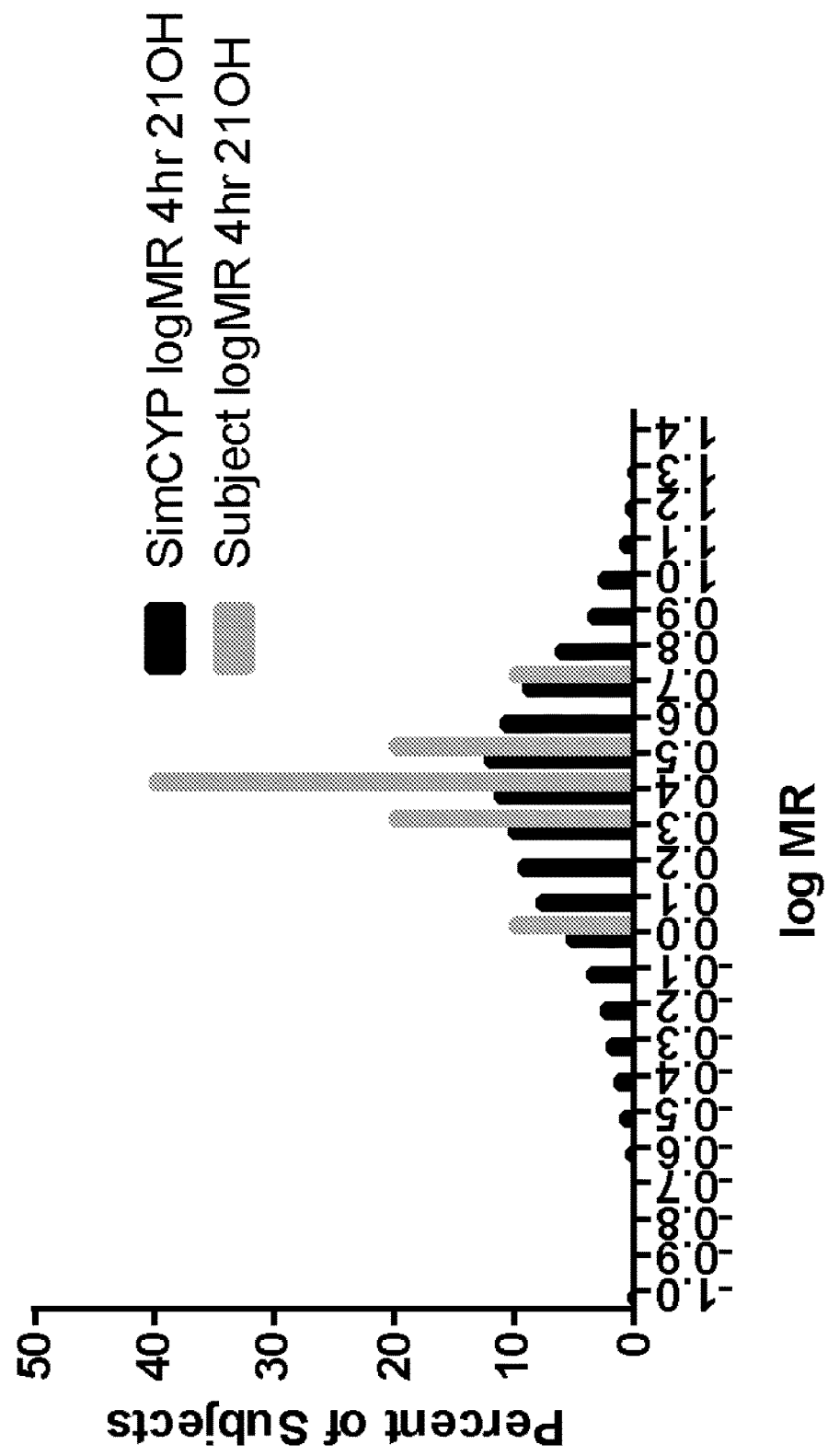

SimCYP provided an excellent platform to validate our model of salivary eplerenone as a probe for CYP3A4/5 activity. We created a SimCYP model (see Table 1.) and were able to model plasma concentrations while using unbound plasma concentrations as a surrogate for salivary concentrations. The model also allowed us to identify the optimal timing for metabolic ratio measurements. Based on the SimCYP derived data obtained in Table 2., 4 hours was selected as the optimal timing for saliva determination of metabolic phenotype. The correlation between unbound AUC (a surrogate for salivary AUC) and the log values of the various phenotypic metrics (EP4hr, 6OH-EP, and 21OH-EP) was highest at 4 hours for EP4 hr (r=0.99), and 6OH-EP (r=0.92). The 4 hour correlation was slightly lower for 21-OH EP (r=0.89), but essentially identical to the peak correlation at 5 hours (r=0.90), 4 hours was chosen as the optimal time for metabolic ratio determination. Validation of the SimCYP model was performed using plasma eplerenone concentrations published by Cook et al. in addition to salivary data we collected. Good data fit) was established between modeled data and clinical data (see FIGS. 1,2,3).

Table 4 shows the Spearman correlations between the eplerenone metabolic phenotype metrics (log EP 4 hr, log 6OH MR, and log 21OH MR) and SimCYP derived CYP3A substrate PK parameters (log AUC and log CLint). The right of the table describes the percent contribution of CYP3A to the metabolism of each substrate, the relative contribution of CYP3A5, and whether or not the contribution of CYP3A5 to clearance was included in the SimCYP model.

The correlations between phenotypic metrics and PK parameters should follow similar trends since CL=F*D/AUC. When comparing correlations between phenotypic metrics and PK parameters, higher correlations were found for $CL_{int}$. This was expected since $CL_{int}$ calculations are derived directly from imputed values of hepatic clearance in SimCYP. Log EP 4 hr was consistently the phenotypic marker with the highest correlations to both AUC and $CL_{int}$. This was an unexpected finding but has been observed with midazolam as well (Mueller and Drewelow 2013). Even though the 4 hr eplerenone concentration carried the highest correlation, we suspected it was not the best measure of hepatic CYP3A5 activity, because the majority of eplerenone clearance is mediated through CYP3A4 conversion to the 6O-hydroxy metabolite.

Another important trend in Table 4 is higher correlations with the log 21OH MR when; 1) SimCYP models include CYP3A5 contributions to metabolism and 2) The contribution of CYP3A5 is significant (greater than 14% based on data in Table 4). In the cases where CYP3A5 is not included in the SimCYP model, it is impossible to determine its relative contribution to metabolism. Therefore, we had to rely on the CYP3A4/5 substrates in the upper part of Table 4 for comparison. Of those, CYP3A5 plays a significant role in midazolam and triazolam metabolism. For triazolam and midazolam, log 21OH MRs correlates strongly (r>0.8) with AUC and CLint. Log EP4 hr MR vs. AUC correlation coefficients for midazolam and triazolam (0.83 and 0.85 respectively) are very close to the log 21OH MRs vs. AUC correlations (0.82 and 0.82 respectively). Conversely, alprazolam and nifedipine have low contributions from CYP3A5 to their clearance. As expected, they show lower correlations for the log 21OH MR vs. AUC (0.66 and 0.70) in comparison to the log EP 4hr vs. AUC (0.81 and 0.77). Based on the findings, we observed that log EP4 hr is the best phenotypic metric for substrates predominately metabolized by CYP3A4 (<=14% contribution of CYP3A5). Despite having the highest correlations with AUC, log EP4 hr is biased toward CYP3A4 metabolism because eplerenone is predominantly metabolized via CYP3A4. Conversely, CYP3A4 and CYP3A5 make similar contributions to the 21OH metabolite formation. Therefore, log 21OH MR is a better phenotypic metric for substrates metabolized by both CYP3A4 and CYP 3M.

Figure 4A:
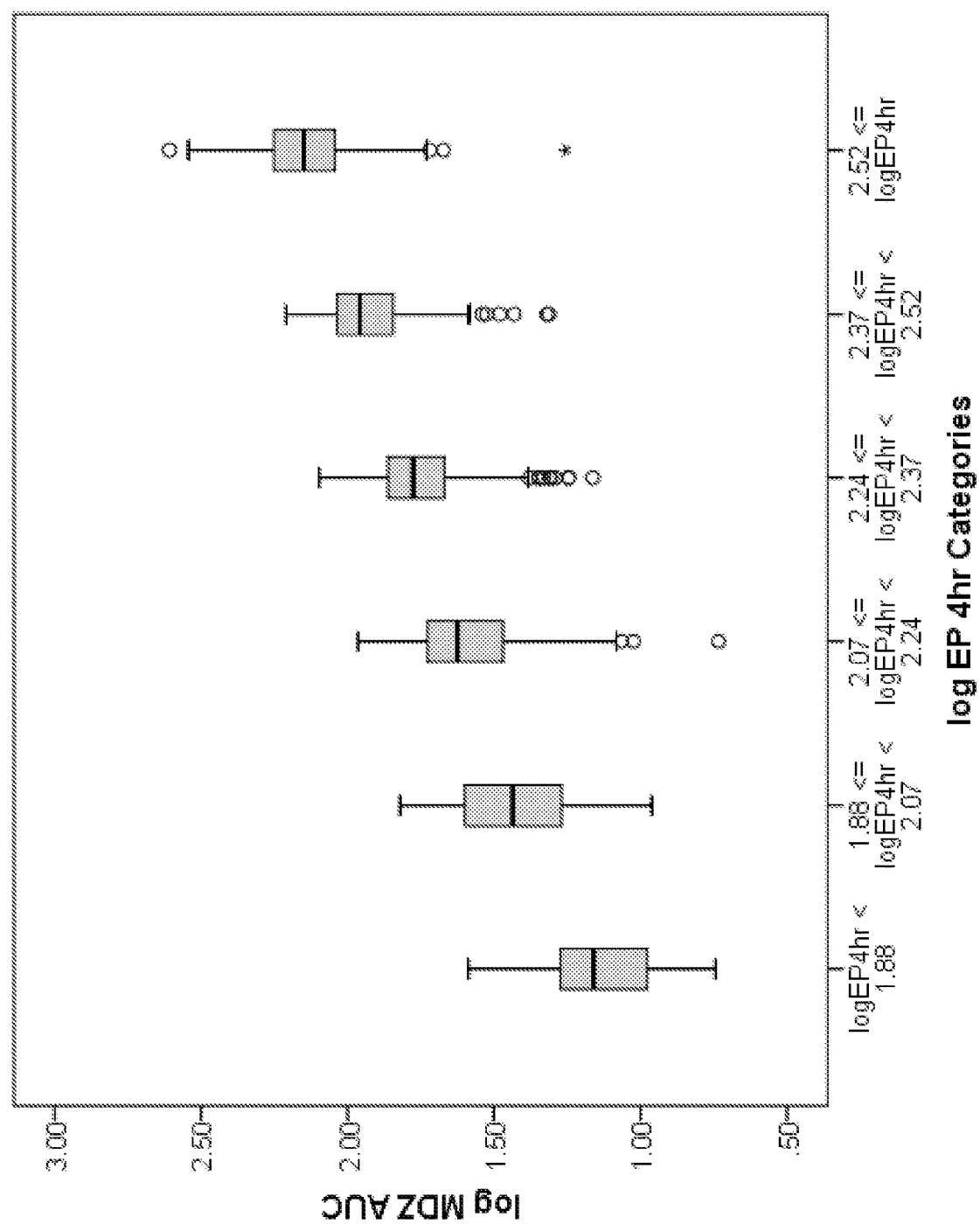
FIGS. 4A, 4B, and 4C show optimized phenotyping categories for log midazolam AUC versus log eplerenone (EP) 4 hr (FIG. 4A), log midazolam AUC versus log 6β-hydroxyeplerenone (6OH) 4 hr (FIG. 4B), and log midazolam AUC versus log 21-hydroxyeplerenone (21OH) 4 hr (FIG. 4C).
Figure 4B:
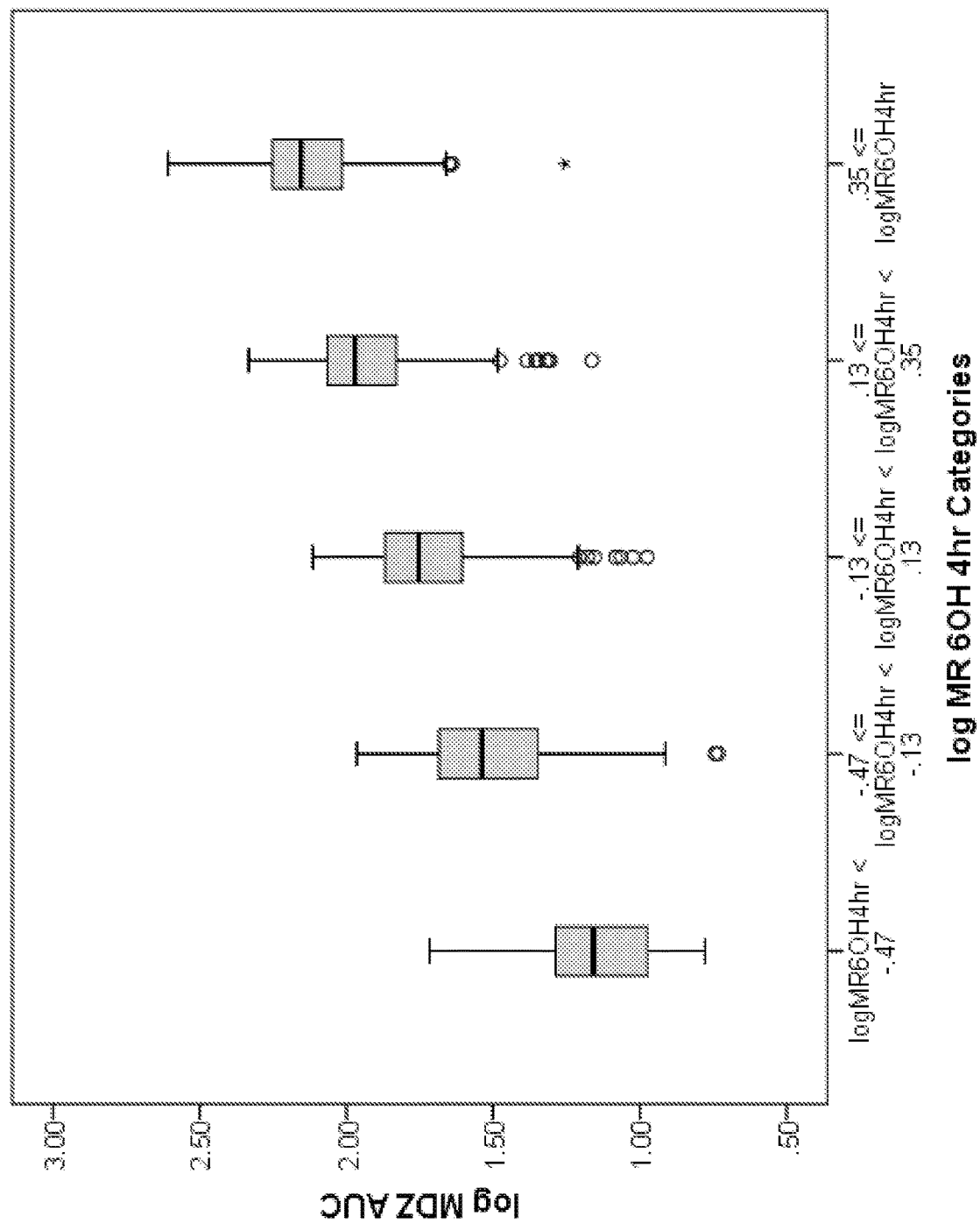
Figure 4C:
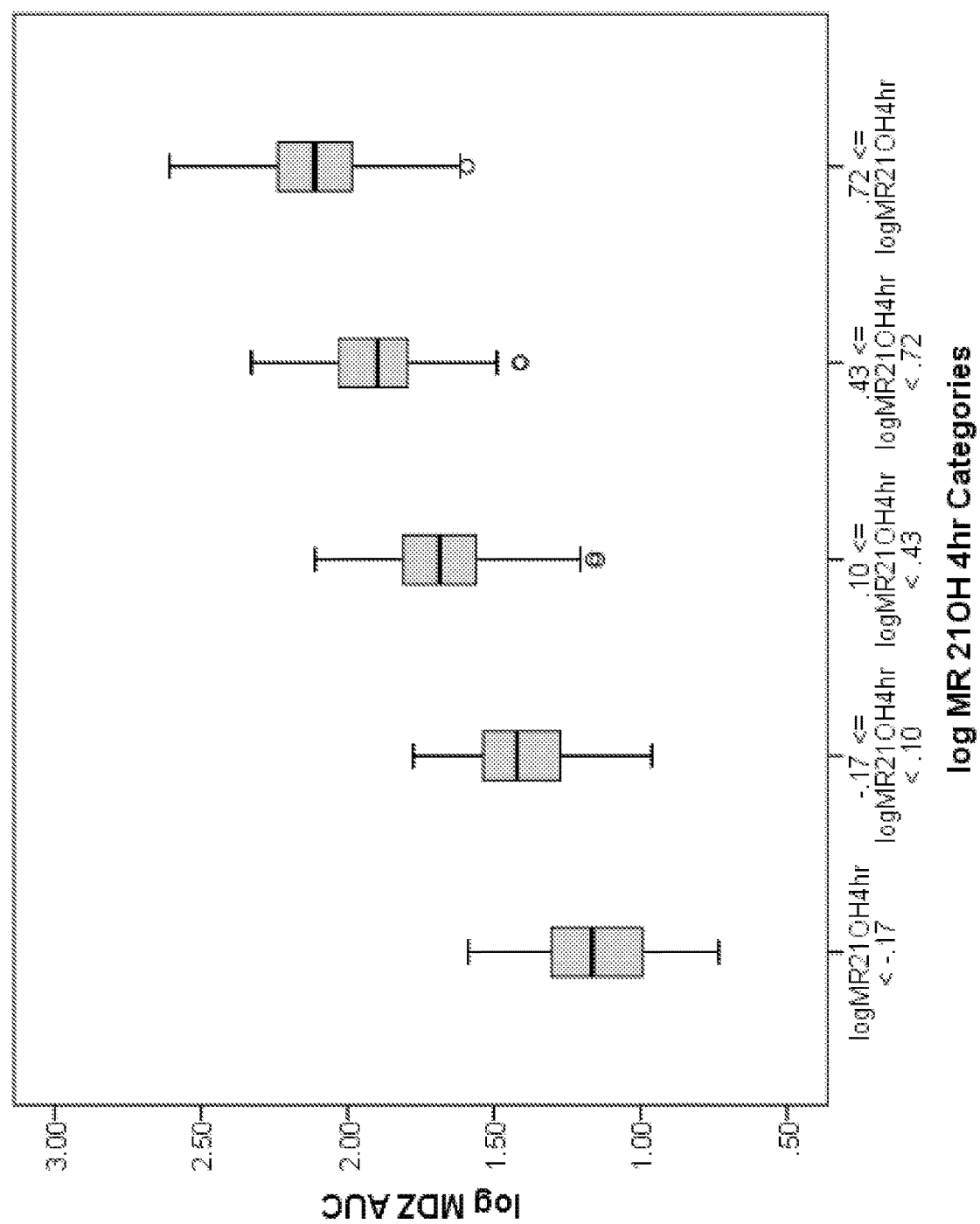
Figure 5A:
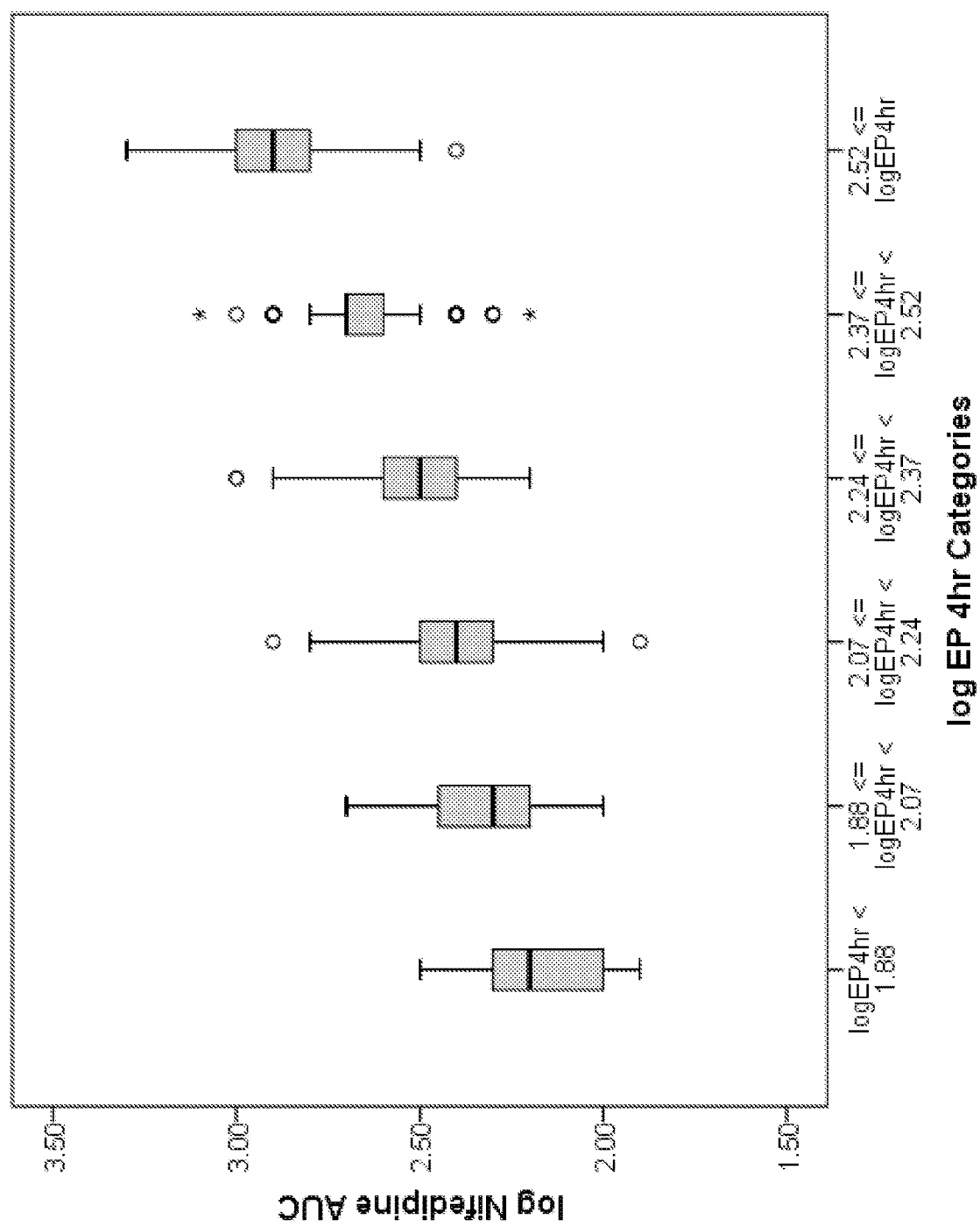
FIGS. 5A, 5B, and 5C show optimized phenotyping categories for log nifedipine AUC versus log eplerenone (EP) 4 hr (FIG. 5A), log nifedipine AUC versus log 6β-hydroxyeplerenone (6OH) 4 hr (FIG. 5B), and log nifedipine AUC versus log 21-hydroxyeplerenone (21OH) 4 hr (FIG. 5C).
Figure 5B:
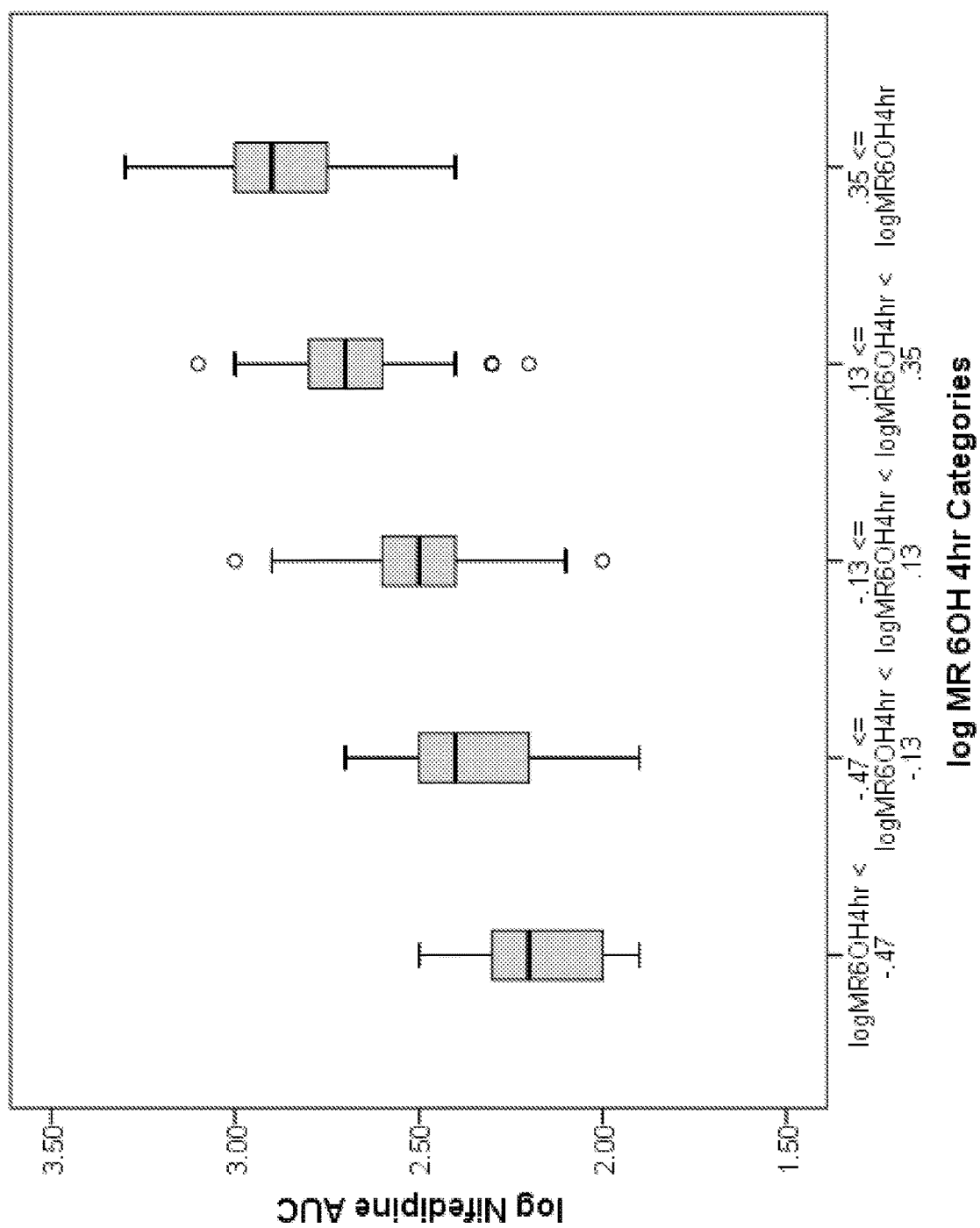
Figure 5C:
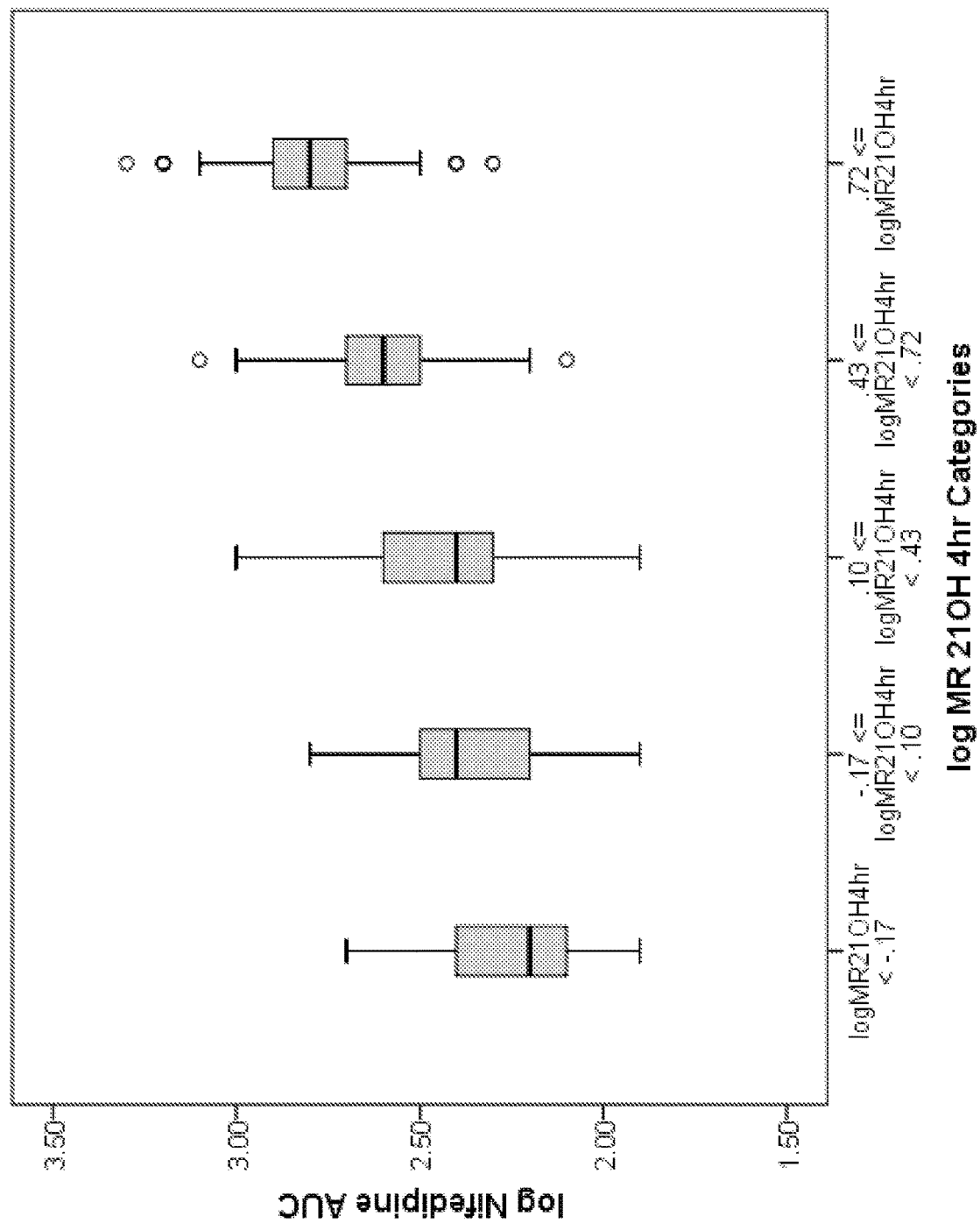

Boxplots comparing categorical phenotypic metrics and AUC confirmed our hypotheses. For midazolam, a prototypical CYP3A4/5 probe, log 21OH MR proved to be the best phenotypic metric (FIGS. 4a, 4b, 4c). For nifedipine, a prototypical CYP3A4 only probe, EP4 hr was the best phenotypic metric (FIGS. 5a, 5b, 5c). Boxplots representing optimized categorical groupings of phenotypic metrics followed a linear pattern with respect to midazolam and nifedipine AUC. The optimal phenotypic probes, log 21OH MR for midazolam (see FIGS. 4c), and 4 hr EP for nifedipine (see FIG. 5c) carried the lowest variance for the boxes in the plot and also had the least outliers per box.

Consideration of the extreme boxes to the left and right of the boxplot allow for comparison of individuals at the extremes of CYP3A4/5 and CYP3A4 clearance. Starting with midazolam AUC and its optimal phenotypic metric 21OH-EP (measure of CYP3A4/5 phenotype). The leftmost box in FIG. 4c. corresponds to a log 21OH of <−0.17 and a mean AUC of 14 (±0.3). The number of subjects in this leftmost category is 6.2% of subjects. The mean for the rightmost box in FIG. 4c. corresponds to a log 21OH of >0.72 and an AUC of 128 (±0.9). The number of subjects in this rightmost category is 15.4% of subjects. The mean AUC for midazolam was 57 (±10). Therefore, individuals in the first category have AUCs 4.1 fold lower than the mean on average, while individuals in the rightmost category have 2.3 fold higher than average AUCs.

For nifedipine AUC and its optimal phenotypic metric EP 4 hr (measure of CYP3A4 phenotype). The mean for the leftmost box in FIG. 5a. corresponds to a log EP4 hr of <1.88 and a mean AUC of 146 (±1.7). The number of subjects in this leftmost category is 4.9% of subjects. The mean for the rightmost box in FIG. 5a. corresponds to a log EP4 hr ≥2.52 and a mean AUC of 713 (±3.3). The number of subjects in this rightmost category is 14.2% of subjects. The mean AUC for nifedipine was 346 (±32). In this case, individuals in the first category have AUCs 2.4 fold lower than the mean on average, while individuals in the rightmost category have 2.1 fold higher than average AUCs.

These findings highlight the value of 21OH-EP MR as a marker of CYP3A4/5 activity. 21OH-EP MR categories were the best phenotypic markers of midazolam exposure because midazolam is metabolized by CYP3A4 and CYP3A5. Conversely, the 21OH-EP MR was not the best marker for nifedipine because nifedipine is metabolized almost exclusively by CYP3A4. In the case of nifedipine, EP4hr exhibited the best association with AUC.

Conclusion

Utilizing SimCYP, we were able to create a model of eplerenone as a substrate probe for CYP3A4 and CYP3A4/5. The SimCYP model shows good agreement with clinical data. SimCYP models allowed optimization of the timing of MR measurements and gave excellent estimates of population level variability. Using existing data and SimCYP models for other CYP3A substrates we identified 21OH EP 4hr as an ideal phenotyping metric for CYP3A substrates that are metabolized by CYP3A4 and CYP3A5. For substrates metabolized predominantly by CYP3A4, the EP 4hr metric is the best phenotypic metric.

We have identified salivary eplerenone metabolic phenotyping as a rapid, simple, and robust tool to determine CYP3A4 and CYP3A4/5 activity on an individual and population level. Future work will be aimed at identifying the relationship between eplerenone MR, dosing of other CYP3A4/5 substrates, and clinical outcomes.

References

Cook, C. S., L. M. Berry, R. H. Bible, J. D. Hribar, E. Hajdu and N. W. Liu (2003). "Pharmacokinetics and metabolism of [14C]eplerenone after oral administration to humans." Drug Metab Dispos 31(11): 1448-1455.

Galetin, A., C. Brown, D. Hallifax, K. Ito and J. B. Houston (2004). "Utility of recombinant enzyme kinetics in prediction of human clearance: impact of variability, CYP3A5, and CYP2C19 on CYP3A4 probe substrates." Drug Metab Dispos 32(12): 1411-1420.

Hohmann, N., W. E. Haefeli and G. Mikus (2016). "CYP3A activity: towards dose adaptation to the individual." Expert Opin Drug Metab Toxicol 12(5): 479-497.

Ingelman-Sundberg, M. (2004). "Human drug metabolising cytochrome P450 enzymes: properties and polymorphisms." Naunyn Schmiedebergs Arch Pharmacol 369(1): 89-104.

Lee, L. S., J. S. Bertino and A. N. Nafziger (2006). "Limited sampling models for oral midazolam: midazolam plasma concentrations, not the ratio of 1-hydroxymidazolam to midazolam plasma concentrations, accurately predicts AUC as a biomarker of CYP3A activity." J Clin Pharmacol 46(2): 229-234.

McGraw, J. (2014). Chapter 16 - CYP450 and Ethnicity A2 -Padmanabhan, Sandosh. Handbook of Pharmacogenomics and Stratified Medicine. San Diego, Academic Press: 323-340.

Mezzullo, M., A. Fazzini, A. Gambineri, G. Di Dalmazi, R. Mazza, C. Pelusi, V. Vicennati, R. Pasquali, U. Pagotto and F. Fanelli (2017). "Parallel diurnal fluctuation of testosterone, androstenedione, dehydroepiandrosterone and 17OHprogesterone as assessed in serum and saliva: validation of a novel liquid chromatography-tandem mass spectrometry method for salivary steroid profiling." Clin Chem Lab Med.

Mueller, S. C. and B. Drewelow (2013). "Evaluation of limited sampling models for prediction of oral midazolam AUC for CYP3A phenotyping and drug interaction studies." Eur J Clin Pharmacol 69(5): 1127-1134.

Patki, K. C., L. L. Von Moltke and D. J. Greenblatt (2003). "In vitro metabolism of midazolam, triazolam, nifedipine, and testosterone by human liver microsomes and recombinant cytochromes p450: role of cyp3a4 and cyp3a5." Drug Metab Dispos 31(7): 938-944.

Penzak, S. R., K. H. Busse, S. M. Robertson, E. Formentini, R. M. Alfaro and R. T. Davey (2008). "Limitations of using a single postdose midazolam concentration to predict CYP3A-mediated drug interactions." J Clin Pharmacol 48(6): 671-680.

Wilkinson, G. R. (2005). "Drug metabolism and variability among patients in drug response." N Engl J Med 352(21): 2211-2221.

Example 2

The Relative Role of CYP3A4 and CYP3A5 in Eplerenone Metabolism

Introduction

Eplerenone is an aldosterone antagonist used to treat heart failure. Aldosterone antagonism results in anti-mineralocorticoid effects similar to potassium sparing diuretics such as spironolactone. Liver CYP450 mediated metabolism is the primary route of eplerenone elimination with small amounts of a lactone degradation product and unchanged parent excreted via the kidney. Several CYP450 derived hydroxylated metabolites are formed. However, 6β-hydroxy eplerenone is the primary metabolite with 21-hydroxy eplerenone being the second most abundant metabolite. The CYP3A family is responsible for eplerenone's oxidative metabolism. In-vitro human metabolism studies show CYP3A4 generates the 6β-hydroxy eplerenone metabolite with minimal contribution via CYP3A5 (Cook, Berry et al. 2002, Cook, Zhang et al. 2003). However, the relative contribution of CYP3A5 to the 21-hydroxy metabolite is unknown. We performed in-vitro experiments with recombinant CYP 3A4 (rhCYP3A4) and CYP3A5 (rhCYP3A5) to delineate the relative contribution of CYP3A4 and CYP3A5 to generation of the 21-hydroxy eplerenone metabolite. Although CYP3A4 and CYP3A5 have high homology and substrate specificity, their relative contributions to generating the 6β-hydroxy metabolite and 21-hydroxy metabolite might not be the same. Eplerenone paired with its 6β-hydroxy metabolite form the basis of a specific substrate probe for CYP3A4 activity in-vitro and in-vivo. Surprisingly, we found no previous publications using eplerenone as a substrate probe. Selective formation of the 21-hydroxy metabolite via CYP3A4 and CYP3A5 may differ from the 6β-hydroxy metabolite. If this is found, eplerenone's use as a probe could be extended even further.

Materials and Methods

Chemicals and Reagents. Eplerenone was obtained from Chem-Impex International and United States Pharmacopeia (USP), potassium phosphate buffer (KPO4), methanol (MS grade), acetonitrile (MS grade), and water (MS grade) were purchased from Sigma-Aldrich (St. Louis, Mo.). Pooled human liver microsomes from 150 donors (HLM150) and individual recombinant CYP450 3A4 and 3A5+b5 enzymes (Supersomes™) and NADPH regeneration solutions were obtained from BD Biosciences/Corning (Corning, N.Y.).

Incubation Conditions and Sample Preparation. Incubations were performed combining substrate, NADPH regeneration solution, and potassium phosphate buffer to obtain a final reaction volume of 200 mcl. A sufficient quantity of 0.05M potassium phosphate buffer was combined with 10 mcl of 20 mg/ml HLM 150 or 5 mcl of rhCYP3A4+b5 and rhCYP3A5+b5, 20 mcl NADPH regenerating solution A, and 5 mcl NADPH regenerating solution B to obtain a volume of 198 mcl in a 1.5ml microcentrifuge tube. The reaction mixture was heated to 37°0 C. in an Eppendorf thermomixer. Reactions were initiated by the addition of 2 mcl of substrate solutions.

Final eplerenone substrate concentrations in solution were 362 mcM, 241 mcM, 121 mcM, 60 mcM, 30 mcM, 15 mcM and 7.5 mcM. Reactions were initiated by the addition of substrate. Incubation time was 10 minutes, temperature was held at 37° C., and the thermomixer was set to 300 rpm. Controls included reaction mixtures without NAPDH regenerating solution and mixtures without supersomes.

Incubations were stopped by the addition of 300 mcl ice cold ACN/0.1% formic acid. The incubations were centrifuged at 8500 rpm for 10 minutes in a microcentrifuge. The incubation mixtures were then transferred to HPLC vials, spiked with 5 mcl of 4 mcg/ml diazepam internal standard, and loaded onto the UHPLC.

Multipliers used in sample reaction rates for recombinant microsomes were (ng/ml)*[0.2 ml reaction volume]/[metabolite M.W. (430.19 ng/nmol)]*[5/2 (Dil Factor)]*[1000 pmol/nmol]/[5 pmol enzyme]/[10 min]*[pmol of rhCYP3A4 (196 pmol/mg) or rhCYP3A5/mg (182 pmol/mg) supersomes]. Multipliers used in sample reaction rates forHLM were (ng/ml )*[0.2 ml reaction volume]/[metabolite M.W. (430.19 ng/nmol)]*[5/2 (Dil Factor)]*[1000 pmol/nmol]/[0.2 mg HLM protein]/[10 min].

UHPLC MS/MS Methods. Chemical analysis was performed by a Sciex 4000 Qtrap and Dionex RSLC 3000 UHPLC. Solution A consisted of water with 5% MeOH, 0.05% acetic acid, and solution B contained 35% acetonitrile, 65% MeOH, with 0.05% acetic acid. The Acquity UHPLC HSS T3 1.8 mcm, 2.1*50 mm column was equilibrated with 50% B for 0.2 min then changed to 95% B 0.35 minutes after injection and ramped from 95% B at 0.35 min to 100% B at 2.75 min, which was held for 0.75 minutes.

Using APCI positive mode, Curtain gas 30, Source Temperature 400° C., Source gas 1 80 psi, gas 2 60 psi, collision gas high, ion spray voltage 5500 V. Analyte MRMs with DP and CE were: Eplerenone (415/163 DP 60, CE 30, CXP 10), 6β-hydroxy Eplerenone (431/211 DP 60, CE 20, CXP 10), 21-hydroxy Eplerenone (431/163 DP 60, CE 20, CXP 10), and Diazepam (285/193 DP 90, CE 45, CXP 13).

Enzyme Kinetics. The data were fit to curves using non-linear iterative (1000) fitting in GraphPad Prism 6 for Michaelis-Menton and Substrate Inhibition with parameter estimation. Intersystem extrapolation factor (ISEF) can be obtained from the equation, Equation 1.

$$ISEF = \frac{CL_{int}HLM}{CL_{int}rhCYP450} = \frac{V_{max}/Km\ HLM}{V_{max}/Km\ rhCYP450 \times CYP450\ \text{abundance in}\ HLM}.$$

The ISEF was calculated by summing the HLM 6β-hydroxy metabolite clearance and the 21-hydroxy metabolite clearance and dividing by the sum of rhCYP3A4 metabolite clearances multipled by the abundance in HLM 150 (71pmol/mg) and rhCYP3A5 metabolite clearances multipled by the abundance in HLM 150 (10 pmol/mg). We used the following equation (Eq.2) to calculate fractional metabolism ($f_m$) of the metabolites via CYP3A4 and CYP3A5, $$f_m = \frac{V_{max}/Km\ rhCYP450\ \text{isoform} \times CYP450\ \text{abundance in}\ HLM}{\sum V_{max}/Km\ rhCYP450\ \text{isoforms} \times CYP450\ \text{abundance in}\ HLM}.$$

Results

Figure 6:
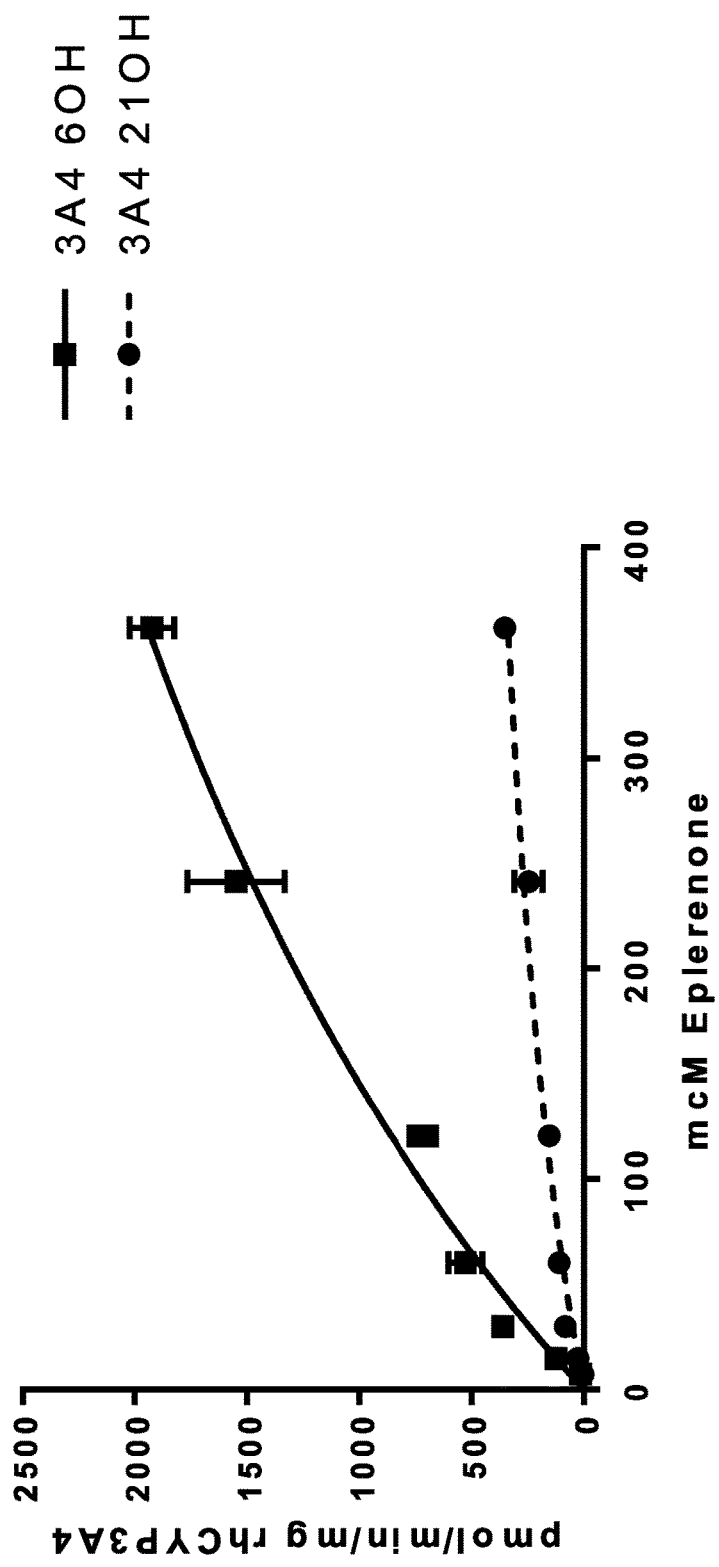
FIG. 6 shows eplerenone metabolism via rhCYP3A4.

Microsomal incubations with rhCYP3A4 and rhCYP3A5 enzymes gave similar results to previous reports using human liver microsomes (Cook 2002). Results of rhCYP3A4 incubations presented in FIG. 6 and Table 6 agree with previous findings by Cook et al. that production of the 6β-hydroxy metabolite is primarily mediated by CYP3A4.

TABLE 6

Eplerenone Metabolism Kinetic Parameters

| Microsome/Metabolite | Microsome Source | Vmax (pmol/min/mg) | Km (mcM) | Vmax/km |
|---|---|---|---|---|
| HLM 6β-OH | Xenotech* | 973 | 217 | 4.5 |
| HLM 21-OH | Xenotech* | 143 | 211 | 0.68 |
| HLM 150 6β-OH | Corning/BD | 1493 | 473 | 3.2 |
| HLM 150 21-OH | Corning/BD | 216 | 197 | 1.1 |

| Metabolite | Recombinant CYP450 | Vmax (pmol/min/mg) | Km (mcM) | Vmax/km |
|---|---|---|---|---|
| 6β-OH | rhCYP3A4 | 5232 | 613 | 8.5 |
|  | rhCYPA5 | 290 | 142 | 2.0 |
| 21-OH | rhCYP3A4 | 436 | 362 | 1.2 |
|  | rhCYP3A5 | 154 | 72 | 2.1 |

| Metabolite | Recombinant CYP450 | Vmax (pmol/min/pmol CYP) | Km (mcM) | Vmax/km |
|---|---|---|---|---|
| 6β-OH | rhCYP3A4 | 28.8 | 613 | 0.0469 |
|  | rhCYPA5 | 1.5 | 142 | 0.0104 |
| 21-OH | rhCYP3A4 | 2.4 | 362 | 0.0066 |
|  | rhCYP3A5 | 0.79 | 72 | 0.0109 |

*Reported by Cook et al. 2002

Figure 7:
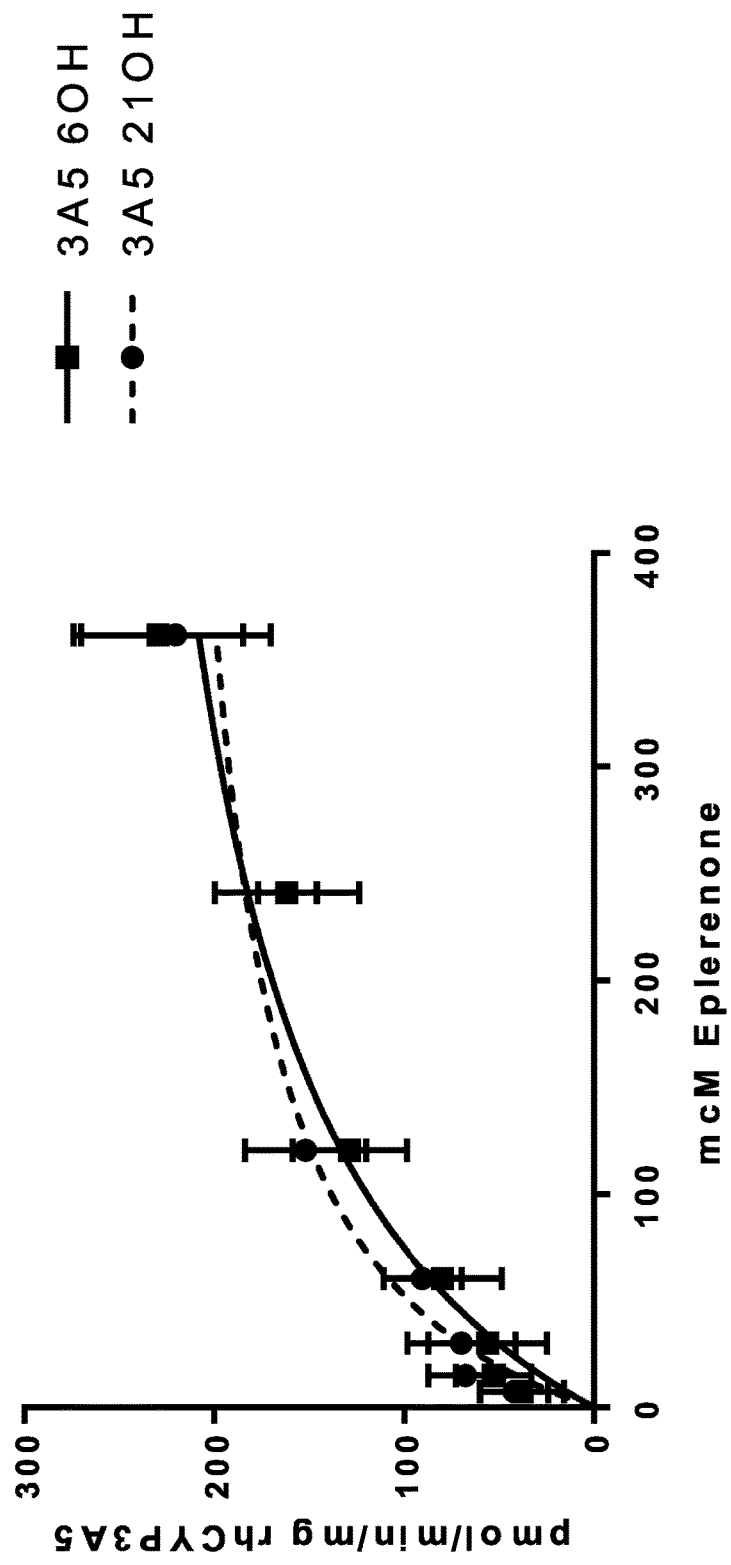
FIG. 7 shows eplerenone metabolism via rhCYP3A5
Figure 8:
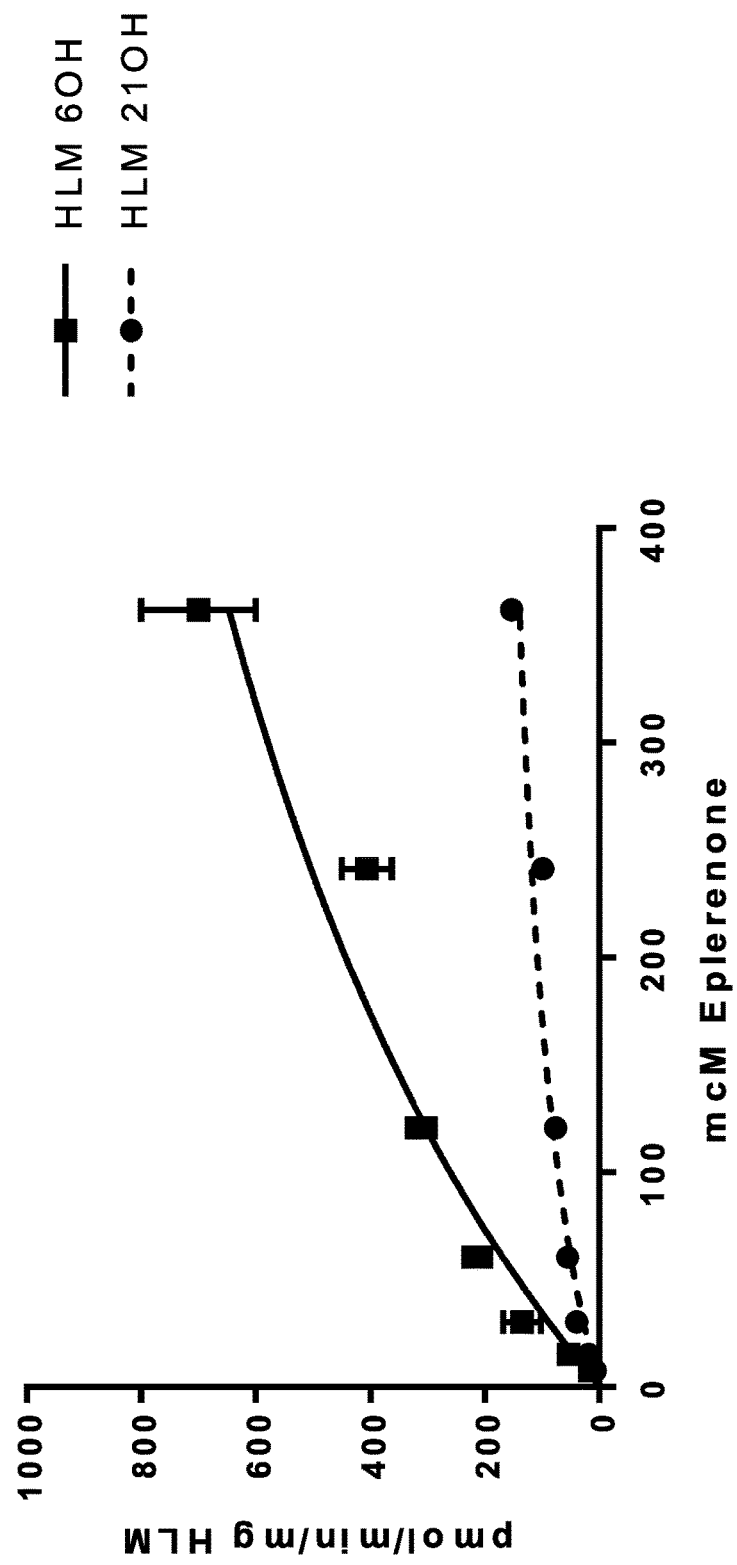
FIG. 8 shows eplerenone metabolism via human liver microsomes.

FIG. 7 shows similar enzyme kinetics for the 6β-hydroxy metabolite and 21-hydroxy-eplerenone when generated by CYP3A5. However, the 6β-hydroxy metabolite is generated at a higher Vmax than the 21-hydroxy metabolite while the km was significantly lower for the 21-hydroxy metabolite. FIG. 8 shows the enzyme kinetics for HLM150 pooled human liver microsome generation of the 6β-hydroxy metabolite and 21-hydroxy metabolites.

The data in Table 6 allows scaling of metabolism via HLM and recombinant systems. (See Eq. 1 and Table 6). The ISEF for recombinant CYP3A4/5 was found to be 1.0. Using Eq. 2 along with the recombinant clearances and abundances of enzyme in HLM 150 found in Table 6, we find the fractional metabolism ($f_m$) of the 6β-hydroxy metabolite is 97% via CYP3A4 and 3% via CYP3A5 in HLM 150. The contribution of CYP3A5 towards metabolism of the 21-hydroxy metabolite is much higher. The $f_m$ via CYP3A4 and CYP3A5 are 81% and 19% respectively in HLM 150. If we consider an individual with equal abundances of CYP3A4 and CYP3A5 in their microsomes, say 50 pmol/mg of each, then the $f_m$ for CYP3A4 for the 6β-hydroxy metabolite drops to 82% while the fm for CYP3A4 mediated 21-hydroxy metabolite formation drops dramatically to 38%. This indicates that the 21-hydroxy metabolite formation is predominantly driven by CYP3A5 ($f_m$=62%) for individuals with significant hepatic CYP3A5 expression relative to CYP3A4.

Discussion

Although eplerenone is primarily metabolized by CYP3A4 to the 6β-hydroxy metabolite CYP3A5 makes a small contribution to the overall metabolism. The highly specific metabolism of eplerenone to its 6β-hydroxy metabolite via CYP3A4 makes it an attractive probe substrate for CYP3A4 activity. Currently, testosterone and midazolam are the most commonly utilized probe substrates for CYP3A4 activity (Path, Von Moltke et al. 2003). Several authors have suggested that dual probes should be used to probe CYP3A4 in-vitro activity since it's large active site may accommodate multiple orientations of substrates and allosteric sites are found near the active site (Foti, Rock et al. 2010). An additional complication exists because midazolam and testosterone are both metabolized by CYP3A5 as well as CYP3A4. CYP3A5 has received little attention in the literature until relatively recently because more than 90 percent of Caucasian populations carry a null allele that does not code active enzyme. In addition, CYP3A5 expression in liver is usually significantly lower than CYP3A4. Newer work is shining light on the importance of CYP3A5 (Xiang, Li et al. 2017). Recent work regarding the metabolism of the anti-rejection drug tacrolimus has shown that CYP3A5 can play a significant role in the overall metabolism via CYP3A family enzymes (Woillard, Mourad et al. 2017).

A difficulty in characterizing CYP3A4 and CYP3A5 activity respectively is that all probe drugs have some affinity for both enzymes. Even tacrolimus, which is considered a CYP3A5 specific probe, exhibits significant metabolism via CYP3A4. In a study by (Kamdem, Streit et al. 2005), CYP3A5 activity was only important for tacrolimus metabolism when individuals expressed low amounts of CYP3A4 in liver. Tacrolimus Vmax/km values were 0.5 and 0.8 for rhCYP3A4 and rhCYP3A5 respectively. This shows that CYP3A5 has a 60% higher catalytic efficiency via CYP3A5 but the Vmax/km values are on the same order. Vmax/Km values for eplerenone conversion to 21-hydroxy eplerenone via rhCYP3A4 and rhCYP3A5 based on Vmax in pmol/min/mg were 1.9 and 3.3 respectively, indicating a 74% higher catalytic efficiency for CYP3A5 in mediating the conversion to the 21-hydroxy metabolite. Although CYP3A4 has a significant role in 21-hydroxy eplerenone formation CYP3A5 plays a more significant role when it is expressed signficantly. This is in contrast to eplerenone 6β-hydroxy conversion which is highly specific to CYP3A4. The CYP3A4 mediated 6β-hydroxy eplerenone metabolic efficiency is 425% higher than for CYP3A5. CYP3A4/5 exhibits a lower extraction ratio and catalytic efficiency with a higher km for eplerenone compared to the gold standard clinical probe midazolam. Eplerenone has several advantages over midazolam as a probe drug because midazolam can inhibit metabolism of other CYP3A4/5 substrates, it is a controlled substance, and its clearance is limited by blood flow rather than enzyme activity for individuals with robust enzyme activity (Streetman et al. 2000).

In summary, eplerenone forms two major hydroxylated metabolites via CYP3A4 and CYP3A5. The 6β-hydroxy metabolite exhibits a strong preferential metabolism via CYP3A4 while the 21-hydroxy metabolite exhibits a more modest preferential metabolism via CYP3A5. This duality in metabolite production may allow probing enzyme activity of CYP3A4 alone via the 6 beta-hydroxy metabolite and the combination of CYP3A4/5 through the 21-hydroxy metabolite. Eplerenone is unlikely to interact with other CYP3A4 substrates due to a high $IC_{50}$ (>300 mcM) (Cook et al. 2002). Additionally, hepatic blood flow will not be the rate limiting factor for eplerenone as it is with some individuals taking midazolam. These attributes make eplerenone an excellent substrate probe for future clinical study of CYP3A4 and CYP3A4/5 activity.

References

Cook, C. S., L. M. Berry, D. H. Kim, E. G. Burton, J. D. Hribar and L. Zhang (2002). "Involvement of CYP3A in the metabolism of eplerenone in humans and dogs: differential metabolism by CYP3A4 and CYP3A5." Drug Metab Dispos 30(12): 1344-1351.

Cook, C. S., L. Zhang, G. B. Ames, J. Fischer, J. Zhang and S. Levin (2003). "Single- and repeated-dose pharmacokinetics of eplerenone, a selective aldosterone receptor blocker, in rats." Xenobiotica 33(3): 305-321.

Foti, R. S., D. A. Rock, L. C. Wienkers and J. L. Wahlstrom (2010). "Selection of alternative CYP3A4 probe substrates for clinical drug interaction studies using in vitro data and in vivo simulation." Drug Metab Dispos 38(6): 981-987.

Kamdem, L. K., F. Streit, U. M. Zanger, J. Brockmöller, M. Oellerich, V. W. Armstrong and L. Wojnowski (2005). "Contribution of CYP3A5 to the in vitro hepatic clearance of tacrolimus." Clin Chem 51(8): 1374-1381.

Patki, K. C., L. L. Von Moltke and D. J. Greenblatt (2003). "In vitro metabolism of midazolam, triazolam, nifedipine, and testosterone by human liver microsomes and recombinant cytochromes p450: role of cyp3a4 and cyp3a5." Drug Metab Dispos 31(7): 938-944.

Streetman DS, Bertino JS, Jr. and Nafziger AN (2000) Phenotyping of drug-metabolizing enzymes in adults: a review of in-vivo cytochrome P450 phenotyping probes. Pharmacogenetics 10(3):187-216.

Woillard, J. B., M. Mourad, M. Neely, A. Capron, R. H. van Schaik, T. van Gelder, N. Lloberas, D. A. Hesselink, P. Marquet, V. Haufroid and L. Elens (2017). "Tacrolimus Updated Guidelines through popPK Modeling: How to Benefit More from CYP3A Pre-emptive Genotyping Prior to Kidney Transplantation." Front Pharmacol 8: 358.

Xiang, Q., C. Li, X. Zhao and Y. M. Cui (2017). "The influence of CYP3A5*3 and BCRPC421A genetic polymorphisms on the pharmacokinetics of felodipine in healthy Chinese volunteers." J Clin Pharm Ther 42(3): 345-349.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method comprising:
   (a) administering orally to a subject a composition comprising eplerenone;
   (b) three to four hours after administration, collecting a saliva sample from the subject;
   (c) subjecting the saliva sample to one or more procedures selected from Ultra High Pressure Liquid Chromatography (UHPLC), Mass Spectroscopy (MS), High Pressure Liquid Chromatography (HPLC), Ultraviolet Spectroscopy (UV), Gas Chromatography (GC), Electron Capture Detection (ECD), Flame Ionization Detection (FID), Raman Infrared (RI) Spectroscopy, Matrix-Assisted Laser Desorption/Ionization (MALDI), immunoassay analytical techniques, wherein the procedure provides a saliva concentration of (i) non-metabolized eplerenone;
   (ii) 6β-hydroxyeplerenone; and (iii) 21-hydroxyeplerenone.

2. The method of claim 1, wherein the composition is a tablet formulation of eplerenone, which tablet formulation is coated.

3. The method of claim 2, wherein the tablet formulation is an immediate release tablet formulation of eplerenone.

4. The method of claim 1, wherein the composition that is administered to the subject further comprises caffeine and the method further provides the saliva level of (i) non-metabolized caffeine, and (ii) a caffeine metabolite comprising paraxanthine.

5. The method of claim 1, wherein the composition that is administered to the subject further comprises omeprazole and the method further provides the saliva level of (i) non-metabolized omeprazole, and (ii) a omeprazole metabolite comprising 5OH-omeprazole.

6. The method of claim 1, wherein the composition that is administered to the subject further comprises dextromethorphan and the method further provides the saliva level of (i) non-metabolized dextromethorphan, and (ii) a dextromethorphan metabolite comprising dextrorphan.

7. The method of claim 1, wherein the subject is experiencing or at risk for developing hepatic failure and the method includes assessing hepatic function in the subject.

8. The method of claim 1, wherein the method is performed in order to assess the subject's suitability for a drug study prior to the subject participating in the drug study.

* * * * *

UNITED STATES PATENT AND TRADEMARK OFFICE
CERTIFICATE OF CORRECTION

| | | |
|---|---|---|
| PATENT NO. | : 11,747,352 B2 | Page 1 of 1 |
| APPLICATION NO. | : 16/637153 | |
| DATED | : September 5, 2023 | |
| INVENTOR(S) | : Joseph McGraw et al. | |

It is certified that error appears in the above-identified patent and that said Letters Patent is hereby corrected as shown below:

In the Specification

Column 5, Line 63, "MET$_{cYP3A5}$" should be --MET$_{CYP3A5}$--.

Column 6, Lines 24-25, "MET CYP2D6 CYP2D6" should be --MET$_{CYP2D6}$--.

Column 23, Line 20, "SUB$_c$and" should be --SUB$_{CY3A5}$ and--.

Column 32, Line 15, "6O-hydroxy" should be --6β-hydroxy--.

Column 32, Line 44, "CYP 3M" should be --CYP3A5--.

Signed and Sealed this
Twenty-second Day of April, 2025

Coke Morgan Stewart
*Acting Director of the United States Patent and Trademark Office*